United States Patent
Greff et al.

(10) Patent No.: US 7,053,082 B1
(45) Date of Patent: May 30, 2006

(54) 2,3-BENZODIAZEPINE DERIVATIVES

(75) Inventors: Zoltan Greff, Budapest (HU); Geza Szabo, Budapest (HU); Jozsef Barkoczy, Budapest (HU); Zoltan Ratkai, Budapest (HU); Gabor Blasko, Budapest (HU); Gyula Simig, Budapest (HU); Gabor Gigler, Budapest (HU); Bernadett Martonné Marko, Budapest (HU); György Levay, Budakeszi (HU); Karoly Tihanyi, Budapest (HU); Andras Egyed, Budapest (HU); Annamaria Simo, Budapest (HU)

(73) Assignee: EGIS Gyogyszergyar Rt., Budapest (HU)

( * ) Notice: Subject to any disclaimer, the term of this patent is extended or adjusted under 35 U.S.C. 154(b) by 270 days.

(21) Appl. No.: 10/030,436

(22) PCT Filed: Jul. 4, 2000

(86) PCT No.: PCT/HU00/00074

§ 371 (c)(1),
(2), (4) Date: Mar. 21, 2002

(87) PCT Pub. No.: WO01/04122

PCT Pub. Date: Jan. 18, 2001

(30) Foreign Application Priority Data

Jul. 7, 1999 (HU) .................. 9902291

(51) Int. Cl.
*A61P 25/00* (2006.01)
*A61K 31/551* (2006.01)
*C07D 491/04* (2006.01)

(52) U.S. Cl. ...................... 514/220; 540/557
(58) Field of Classification Search ............... 514/220; 540/557

See application file for complete search history.

(56) References Cited

U.S. PATENT DOCUMENTS 5,756,495 A * 5/1998 Hamori et al. .............. 514/220

* cited by examiner

*Primary Examiner*—Brenda Coleman
(74) *Attorney, Agent, or Firm*—Herbert Dubno; Jonathan Myers

(57) ABSTRACT

The invention relates to new 2,3-benzodiazepine derivatives of general Formula (I), (wherein $R^1$ stands for methyl, formyl, carboxy, cyano, —CH=NOH, —CH=NNHCONH$_2$ or —NR$^5$R$^6$, wherein $R^5$ and $R^6$ independently from each other represent hydrogen or lower alkyl or together with the nitrogen atom, they are attached to, form a 5- or 6-membered, saturated or unsaturated heterocyclic ring optionally containing one or more further nitrogen, sulfur and/or oxygen atom(s); $R^2$ is nitro or amino; $R^3$ stands for hydrogen, lower alkanoyl or CO—NR$^7$R$^8$, wherein $R^7$ and $R^8$ independently from each other stand for hydrogen, lower alkoxy, lower alkyl or lower cycloalkyl or together with the nitrogen atom, they are attached to, form a 5- or 6-membered, saturated or unsaturated heterocyclic ring optionally containing one or more further nitrogen, sulfur and/or oxygen atom(s); $R^4$ is hydrogen or lower alkyl; the dotted lines have the following meaning: if $R^3$ and $R^4$ are not present, the bond between positions $C^8$ and $C^9$ is a single bond and the bond between positions $C^8$ and $N^7$ is a double bond; if $R^3$ and $R^4$ are present, the bonds between positions $C^8$ and $C^9$ and between position $C^8$ and $N^7$ are single bonds; and if $R^3$ is present and $R^4$ is missing, the bond between positions $C^8$ and $C^9$ is a double bond and the bond between positions $C^8$ and $N^7$ is a single bond) and salts thereof. The invention compounds have neuroprotective effect.

21 Claims, 3 Drawing Sheets

2,3-BENZODIAZEPINE DERIVATIVES

CROSS REFERENCE TO RELATED APPLICATION

This application is a 371 of PCT/HU00/00074 filed 4 Jul. 2000.

FIELD OF THE INVENTION

The invention relates to new 2,3-benzodiazepine derivatives, a process for the preparation thereof and pharmaceutical compositions containing the same. More particularly the invention is concerned with 1,3-dioxolo[4,5-h]-[2,3]-benzodiazepines bearing a 4-amino- or -nitro-3-methyl-phenyl-substituent in position 5, a process for the preparation thereof and pharmaceutical compositions containing the same.

STATE OF THE ART

In prior art several biologically active 2,3-benzodiazepine derivatives are described [e.g. HU 155 572, HU 179 018, HU 191 698, HU 191 702, HU 195 788 and HU 206 719]. Said known compounds possess anxiolytic, antidepressant, spasmolytic, muscle relaxant and neuroprotective properties.

Glutamic acid is the most important stimulating neurotransmitter of the central nervous system (stimulating amino acid). The receptors of the glutamic acid neurotransmitter can be divided into two groups, namely ionotropic receptors (attached to the ion channel) and metabotropic receptors. Ionotropic receptors play a role in almost every process of the function of the central nervous system, e.g. the function of learning, all types of memory, processes connected with acute and chronical neurodegeneration and cell deterioration. Said receptors also play a role in pain sensation, motoric functions, urination reflex and cardiovascular homeostasis.

There are two types of ionotropic stimulating receptors, namely receptors of the NMDA and AMPA/cainate type. Receptors of the AMPA/cainate type are responsible in the first place for so-called quick synaptic functions, while NMDA receptors regulate slow synaptic proceedings disposed by quick synaptic processes. Thus receptors of the AMPA/cainate type may indirectly also influence the function of NMDA receptors. It follows from the aforesaid that numerous processes of the central nervous system and the whole organism can be regulated with the aid of antagonists of AMPA/cainate receptors.

There are two types of AMPA/cainate receptor antagonists, namely competitive and non-competitive antagonists. Due to the different character of inhibition, non-competitive antagonists are more favorable than competitive antagonists. The first representative of non-competitive antagonists is 1-(4-amino-phenyl)-4-methyl-7,8-methylenedioxy-5H-2,3-benzodiazepine which was synthetized about 15 years ago. Since the discovery of this compound several non-competitive AMPA/cainate antagonist 2,3-benzodiazepines have been prepared [S. D. Donevan et al.: J. Pharmacol. Exp. Ther., 271, 25–29 (1994); E. S. Vizi et al., CNS Drug Reviews, 2, 91–126 (1996)].

The therapeutical use of 2,3-benzodiazepines which exhibit a non-competitive antagonist effect on the AMPA/cainate receptor is manifold. The 2,3-benzodiazepines synthetized by research chemists of our company can be used as neuroprotective agents in case of symptoms accompanied by all types of acute and chronical neurodegeneration (e.g. Parkinson disease, Alzheimer disease, amyotropic lateral sclerosis, stroke, acute head injuries etc.). In addition to the above applications 2,3-benzodiazepines having AMPA/cainate antagonistic effect can also be used for the treatment of further symptoms, such as epilepsy, as spasmolytics, analgesics, antiemetic agents, against schizophrenia, migraine, urination problems, as anxiolytics, against drug addiction, to alleviate the symptoms of Parkinsonism etc. [I. Tarnawa and E. S. Vizi, Restorative Neurol. Neurosci. 13, 41–57, (1998)].

DESCRIPTION OF THE INVENTION

It is the object of the present invention to provide new 2,3-benzodiazepine derivatives having favorable biological properties.

The above object is solved by the present invention.

According to the present invention there are provided new compounds of the Formula

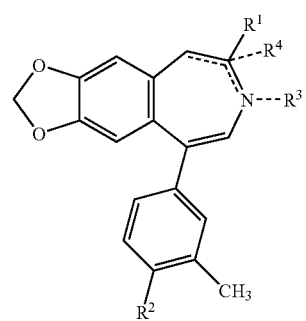

(wherein $R^1$ stands for methyl, formyl, carboxy, cyano, —CH═NOH, —CH═NNHCONH$_2$ or —CO—NR$^5$R$^6$, wherein $R^5$ and $R^6$ independently from each other represent hydrogen or lower alkyl or together with the nitrogen atom, they are attached to, form a 5- or 6-membered, saturated or unsaturated heterocyclic ring optionally containing one or more further nitrogen, sulfur and/or oxygen atom(s);

$R^2$ is nitro or amino;

$R^3$ stands for hydrogen, lower alkanoyl or CO—NR$^7$R$^8$, wherein $R^7$ and $R^8$ independently from each other stand for hydrogen, lower alkoxy, lower alkyl or lower cycloalkyl or together with the nitrogen atom, they are attached to, form a 5- or 6-membered, saturated or unsaturated heterocyclic ring optionally containing one or more further nitrogen, sulfur and/or oxygen atom(s);

$R^4$ is hydrogen or lower alkyl;

the dotted lines have the following meaning:

if $R^3$ and $R^4$ are not present, the bond between positions $C^8$ and $C^9$ is a single bond and the bond between positions $C^8$ and $N^7$ is a double bond;

if $R^3$ and $R^4$ are present, the bonds between positions $C^8$ and $C^9$ and between positions $C^8$ and $N^7$ are single bonds; and if $R^3$ is present and $R^4$ is missing, the bond between positions $C^8$ and $C^9$ is a double bond and the bond between positions $C^8$ and $N^7$ is a single bond)

and pharmaceutically acceptable acid addition salts thereof.

The compounds of the Formula I can be divided into three groups, depending on the double bonds between positions 7,8 and 8,9.

Compounds containing a single bond between positions $C^1$—$C^9$ and a double bond between positions $C^8$—$N^7$ and wherein $R^3$ and $R^4$ are not present, correspond to the Formula

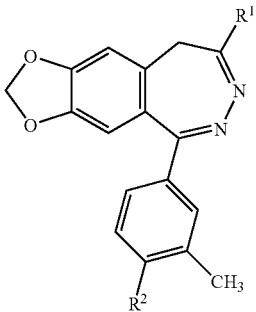

IA (wherein $R^1$ and $R^2$ are as stated above).

Compounds containing single bonds in positions $C^8$—$C^9$ and $C^8$—$N^7$ and wherein $R^3$ and $R^4$ are present, correspond to the Formula

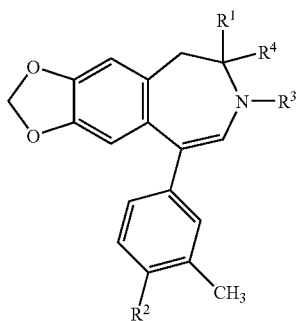

IB wherein $R^1$ and $R^2$ are as stated above).

Compounds containing a double bond between positions $C^8$ and $C^9$ and a single bond in positions $C^8$—$N^7$ and wherein $R^3$ is present and $R^4$ is missing, correspond to the Formula

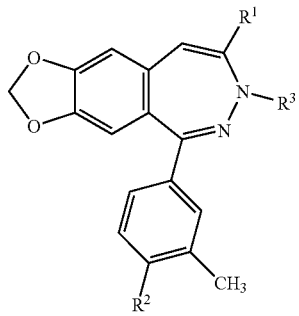

IC wherein $R^1$ and $R^2$ are as stated above).

DETAILED DESCRIPTION OF THE INVENTION

The terms used throughout the patent specification have the following definition.

The term "lower alkyl" relates to straight or branched saturated hydrocarbon groups containing 1–6, preferably 1–4 carbon atoms (e.g. methyl, ethyl, n-propyl, isopropyl, n-butyl, sec. butyl etc.).

The term "lower alkoxy" relates to lower alkyl groups defined above attached through an oxygen atom (e.g. methoxy, ethoxy, n-propoxy, isopropoxy, n-butoxy etc.).

The terms "lower cycloalkyl group" relates to cyclic hydrocarbon groups containing 3–6 carbon atoms (e.g. cyclopropyl, cyclobutyl, cyclopentyl or cyclohexyl).

The term "5- or 6-membered saturated or unsaturated heterocyclic ring optionally containing one or more further nitrogen, sulfur and/or oxygen atom(s)" may be e.g. an imidazole, pyrazole, pyridazine, pyrazine, pyrrolidine, thiazole, thiazine, piperidine, piperazine or morpholine ring etc. Said heterocyclic ring may optionally bear one or more identical or different substituent(s) (e.g. lower alkyl, lower alkoxy, nitro, amino, hydroxy and/or halogen).

The term "pharmaceutically acceptable acid addition salt" relates to salts formed with pharmaceutically acceptable inorganic or organic acids. For salt formation e.g. the following acids can be used: hydrochloric acid, hydrogen bromide, sulfuric acid, phosphoric acid, formic acid, acetic acid, fumaric acid, maleic acid, lactic acid, malic acid, tartaric acid, succinic acid, citric acid, methanesulfonic acid, benzenesulfonic acid etc.

The compounds of the general Formula I contain a chiral carbon atom. The invention encompasses all stereoisomers of the compounds of the Formula I and mixtures thereof, including the racemates.

In case of the presence of certain substituents, the compounds of the Formula I can be present in the form of E- and Z-isomers (tautomery). The invention encompasses all E- and Z-isomers and tautomeric forms of the compounds of the Formula I and mixtures thereof.

A preferred group of the invention compounds are derivatives of the Formula I in which $R^2$ stands for amino.

Compounds of the Formula IB in which $R^2$ stands for amino, possess particularly preferable properties.

A particularly preferred sub group of the compounds of the Formula IB are derivatives in which $R^1$ stands for methyl or cyano; $R^2$ is amino; $R^3$ represents lower alkanoyl or —$CONR^7R^8$; $R^7$ is hydrogen; $R^8$ is lower alkyl, lower alkoxy or lower cycloalkyl and $R^4$ represents hydrogen or methyl.

A particularly preferred representative of the above compounds is the 7-acetyl-5-(4-amino-3-methyl-phenyl)-7,8-dihydro-8-methyl-9H-1,3-dioxolo[4,5-h][2,3]benzodiazepine.

The following compounds of the Formula IB possess valuable properties as well:
5-(3-methyl-4-amino-phenyl)-7-propionyl-7,8-dihydro-8-methyl-9H-1,3-dioxolo[4,5-h][2,3]benzodiazepine;
5-(4-amino-3-methyl-phenyl)-7-(N-cyclopropyl-carbamoyl)-7,8-dihydro-8-methyl-9H-1,3-dioxolo[4,5-h][2,3]benzodiazepine;
5-(4-amino-3-methyl-phenyl)-7-(N-methoxy-carbamoyl)-7,8-dihydro-8-methyl-9H-1,3-dioxolo[4,5-h][2,3]benzodiazepine;
5-(4-amino-3-methyl-phenyl)-7-(N-methyl-carbamoyl)-7,8-dihydro-8-methyl-9H-1,3-dioxolo[4,5-h][2,3]benzodiazepine;

5-(4-amino-3-methyl-phenyl)-7-acetyl-8-cyano-7,8-dihydro-8-methyl-9H-1,3-dioxolo[4,5-h][2,3]benzodiazepine;

5-(4-amino-3-methyl-phenyl)-8-cyano-7-propionyl-7,8-dihydro-8-methyl-9H-1,3-dioxolo[4,5-h][2,3]benzodiazepine.

A further preferable group of the compounds of the present invention are derivatives of the Formula IC in which $R^1$ is methyl; $R^2$ stands for amino; $R^3$ is lower alkanoyl or —CO—$NR^7R^8$; $R^7$ is hydrogen and $R^8$ represents lower alkyl, lower alkoxy or lower cycloalkyl.

Preferred representatives of the compounds of the Formula IC are the following derivatives:

7-acetyl-5-(4-amino-3-methyl-phenyl)-8-methyl-7H-1,3-dioxolo[4,5-h][2,3]benzodiazepine;

7-(N-methyl-carbamoyl)-5-(4-amino-3-methyl-phenyl)-8-methyl-7H-1,3-dioxolo[4,5-h][2,3]benzodiazepine;

7-(N-cyclopropyl-carbamoyl)-5-(4-amino-3-methyl-phenyl)-8-methyl-7H-1,3-dioxolo[4,5-h][2,3]benzodiazepine.

According to a further aspect of the present invention there is provided a process for the preparation of compounds of the Formula I and pharmaceutically acceptable acid addition salts thereof which comprises a) for the preparation of 8-formyl-5-(3-methyl-4-nitro-phenyl)-9H-1,3-dioxolo[4,5-h][2,3]benzodiazepine of the Formula

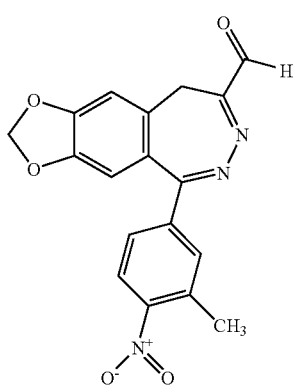

III oxidizing 8-methyl-5-(4-nitro-3-methyl-phenyl)-9H-1,3-dioxolo[4,5-h][2,3]benzodiazepine of the Formula

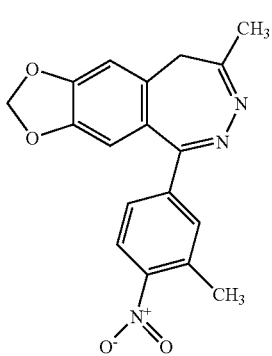

II or b) for the preparation of 5-(3-methyl-4-nitro-phenyl)-9H-1,3-dioxolo[4,5-h][2,3]benzodiazepine-8-carboxylic acid of the Formula

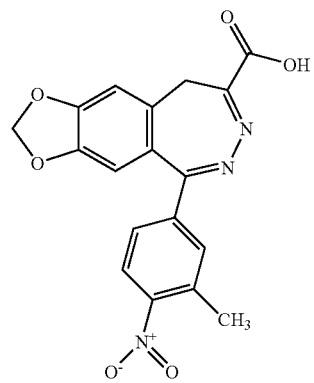

IV oxidizing 8-formyl-5-(3-methyl-4-nitro-phenyl)-9H-1,3-dioxolo[4,5-h][2,3]benzodiazepine of the Formula III;

or c) for the preparation of compounds of the Formula

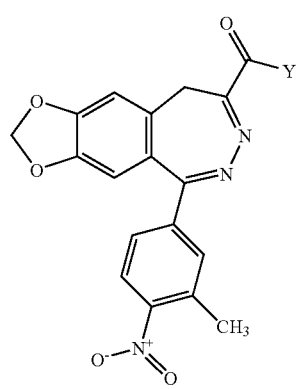

V wherein Y stands for a leaving group), reacting the compound of e Formula IV with a compound capable of introducing group Y; or d) for the preparation of the compound of the Formula

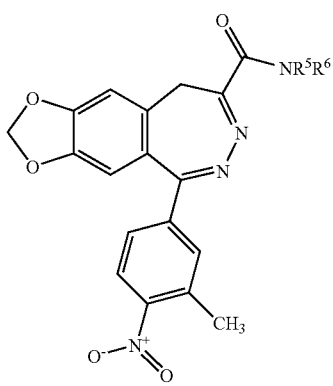

VI wherein R⁵ and R⁶ are as stated above), reacting the carboxylic acid of the Formula IV or a reactive derivative thereof of the Formula V with an amine of the Formula HNR⁵R⁶; or e) for the preparation of compounds of the Formula

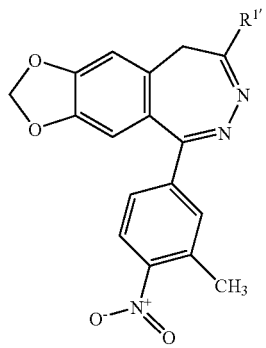

VII wherein R¹' stands for cyano, —CH=NOH or —CH=NNHCONH₂), converting the compound of the Formula III the formyl group into an R¹' group; or f) for the preparation of compounds of the Formula

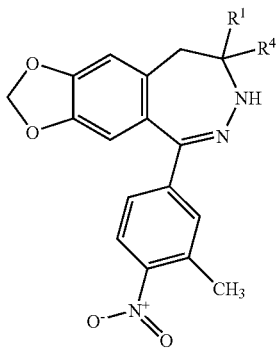

VIII (wherein R¹ and R⁴ are as stated above), saturating the $C^8$—$N^7$ double bond by addition or reduction; or g) for the preparation of compounds of the Formula

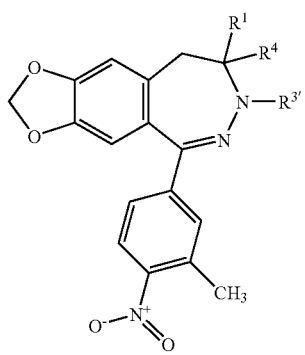

IX (wherein R³' is lower alkanoyl), reacting a compound of the Formula VIII with a compound capable of introducing a lower alkanoyl group; or h) for the preparation of compounds of the Formula

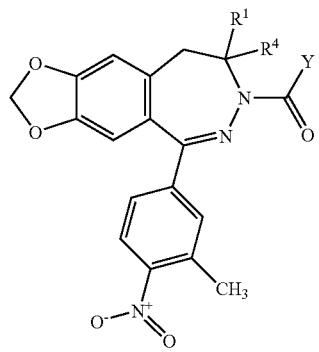

X (wherein Y is a leaving group and R¹ and R⁴ are as stated above), reacting a compound of the Formula VIII with a compound capable of introducing the —COY group; or i) for the preparation of compounds of the Formula

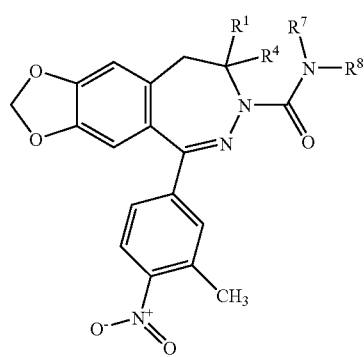

XI (wherein R¹, R⁴, R⁷ and R⁸ are as stated above), reacting a compound of the Formula X or the corresponding free carboxylic acid with an amine of the Formula HNR⁷R⁸; or j) for the preparation of compounds of the Formula

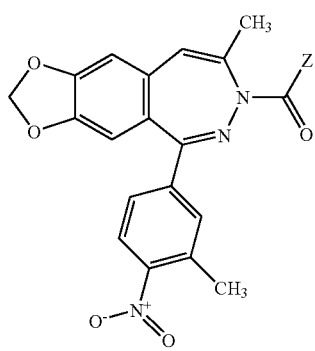

XII (wherein Z stands for a leaving group), reacting the compound of the Formula II with a compound capable of introducing the —COZ group; or k) for the preparation of compounds of the Formula

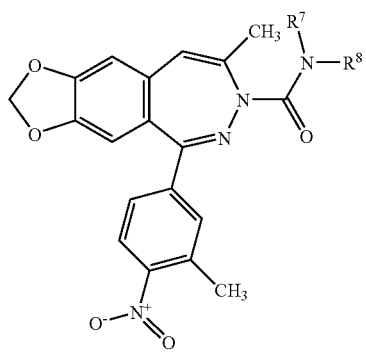

XIII (wherein $R^7$ and $R^8$ are as stated above), reacting a compound of the Formula XII with an amine of the Formula $HNR^7R^8$; or l) for the preparation of compounds of the Formula I, wherein $R^2$ stands for amino, reducing the corresponding compound of the Formula I, wherein $R^2$ is nitro;

and, if desired, converting a compound of the Formula I into a pharmaceutically acceptable acid addition salt thereof or setting free a compound of the Formula I from a salt.

According to process a) in the compound of the Formula II is the methyl group is oxidized into a formyl group to yield a compound of the Formula III. Oxidation may be carried out by methods known per se [Houben-Weyl: Methoden der organischen Chemie, Aldehyde, Band E3, Georg Thieme Verlag, Stuttgart, (1983)]. As oxidizing agent preferably selen(IV)oxide may be used. The compound of the Formula II can be prepared in an analogous manner to HU 191, 702.

According to process b) the formyl compound of the Formula III is oxidized into the carboxylic acid of the Formula IV. Oxidation may be carried out by methods known per se [Houben-Weyl: Methoden der organischen Chemie, Carbonsäure und Carbonsäure-Derivate, Band E5, Georg Thieme Verlag, Stuttgart, (1985); Saul Patai: The chemistry of acid derivatives, John Wiley and Sons, New York]. The reaction may be performed preferably with the aid of silver(I)nitrate in alkaline medium.

According to process c) the compounds of the Formula V are prepared by reacting the carboxylic acid of the Formula IV with an agent capable of introducing the group Y. Said group Y is a suitable leaving group, e.g. halogen (e.g. chlorine or bromine), sulfonyloxy (e.g. alkyl- or aryl-sulfonyloxy, such as methylsulfonyloxy, p-bromo-benzenesulfonyloxy, p-tolyl-sulfonyloxy or benzenesulfonyloxy etc.) or an imidazolyl group. Y represents particularly preferably an imidazolyl group. The process may be carried out by methods known per se [Houben-Weyl: Methoden der organischen Chemie, Carbonsäure und Carbonsäure-Derivate, Band E5, Georg Thieme Verlag, Stuttgart, (1985)]. The imidazolyl group may be introduced by reacting the compound of the Formula IV with 1,1'-carbonyl-diimidazole in a solvent as medium.

According to process d) the amino compounds of the Formula VI are prepared by reacting the carboxylic acid of the Formula IV or a reactive derivative of the Formula V thereof with an amine of the general Formula $HNR^5R^6$. The reaction may be carried out by methods known per se [Houben-Weyl: Methoden der organischen Chemie, Carbonsäure und Carbonsäure-Derivate, Band E5, Georg Thieme Verlag, Stuttgart, (1985); Saul Patai: The chemistry of amide group, Interscience Publishers, 1970)]. It is preferred to use compounds of the Formula V in which Y is imidazolyl.

According to process e) the compounds of the Formula VII are prepared by converting in the compound of the Formula III the formyl group into an $R^{1'}$ group. The process may be carried out by methods known per se [Houben-Weyl: Methoden der organischen Chemie, Carbonsäure und Carbonsäure-Derivate, Band E5, Georg Thieme Verlag, Stuttgart, (1985); Houben-Weyl: Methoden der organischen Chemie, Organische Stickstoff-Verbindungen mit einer C,N-Doppelbindung, Teil 14, Georg Thieme Verlag, Stuttgart, (1990)]. Compounds of the Formula VII, wherein $R^{1'}$ stands for a —CH=NOH group, may be prepared by reacting the compound of the Formula III with hydroxylamine or a salt thereof (e.g. hydrochloride). On treating the product thus obtained with a dehydrating agent a compound of the Formula VII is formed in which $R^{1'}$ stands for cyano. As dehydrating agent preferably methanesulfonyl chloride may be used. The compounds of the Formula VII in which $R^{1'}$ is a —CH=NNHCONH$_2$ group may be prepared by reacting the compound of the Formula III with semicarbazide or a salt (e.g. hydrochloride) thereof.

According to process f) the compounds of the Formula VIII are prepared by saturating the $C^8$—$N^7$ double bond by addition or reduction. According to an embodiment of said process hydrogen cyanide is added on the double bond of the compound of the Formula II. Thus compounds of the Formula VIII are obtained in which $R^1$ is cyano and $R^4$ stands for methyl. According to a further embodiment of this process the $C^8$—$N^7$ double bond of a compound of the Formula II or VI is saturated to yield compounds of the Formula VIII, wherein $R^1$ is methyl or a group of the Formula —CO—$NR^7R^8$. The above reactions may be carried out by known methods [Houben-Weyl: Methoden der organischen Chemie, Band IV, Reduktion, Georg Thieme Verlag, Stuttgart, (1989) or HU 186 760].

According to process g) the compounds of the Formula IX are prepared by reacting a compound of the Formula VIII with an agent capable of introducing a lower alkanoyl group. The process may be carried out by methods known per se. As acylating agent the corresponding acid chlorides, and anhydrides or chloro formiates may be used. The acylation reaction may be performed in the presence of an acid binding agent (e.g. pyridine). The reaction may be carried out at a temperature between –20° C. and 150° C. The reaction may be performed in an organic solvent as medium, whereby an excess of the acylating agent may also act as solvent.

According to process h) the compounds of the Formula X are prepared by reacting a compound of the Formula VIII with an agent capable of introducing a —COY group. Y stands preferably for halogen, alkoxy, aryloxy, imidazolyl, pyrrolidinyl, piperidinyl or 1,2,4-triazolyl, particularly preferably for imidazolyl. The reaction may be carried out by using a hydrogen halide, halogeno formiate or 1,1'-carbonyl-diimidazole, depending on the definition of Y. The reaction may be performed at a temperature between –20° C. and 150° C. The reaction may be carried out in the presence or absence of an acid binding agent (e.g. a pyridine derivative). According to a preferred embodiment of the process the imidazolyl group is introduced into the compound of the Formula VIII with the aid of 1,1'-carbonyl-diimidazole.

According to process i) a compound of the Formula XI is prepared by reacting a compound of the Formula X with an amine of the Formula $HNR^7R^8$. Amination may be carried out by methods known per se [Houben-Weyl: Amine, Bond XI, Georg Verlag, Stuttgart, (1957); S. Patai: The chemistry of amine group, Interscience Publishers, 1968)].

According to process j) the compounds of the Formula XII are prepared by reacting a compound of the Formula II with an agent capable of introducing the group —COZ. Symbol Z stands for a leaving group, preferably halogen, alkoxy or aryloxy. Acylation may be carried out preferably by using the corresponding acid halide, anhydride, 1,1'-carbonyl-diimidazole, hydrogen halide or halogeno formiate. The reaction may be carried out in the presence or absence of an acid binding agent. The reaction temperature is between −20° C. and 150° C. In the course of the reaction the $C^8$—$N^7$ double bond present in the starting material of the Formula II is shifted into position $C^8$—$C^9$.

According to process k) the compounds of the Formula XIII are prepared by reacting a compound of the Formula XII with an amine of the Formula $NHR^7R^8$. The reaction may be carried out by methods known per se [Houben-Weyl: Amine, Bond XI, Georg Verlag, Stuttgart, (1957); S. Patai: The chemistry of amine group, Interscience Publishers, 1968)].

According to process 1) compounds of the Formula I, wherein $R^2$ stands for amino, are prepared by reducing the corresponding compound of the Formula I, wherein $R^2$ stands for nitro. Reduction is preferably carried out by using a nitro compound of the Formula II, VII, IX, XI, XII or XIII. The reaction can be carried out by methods known per se. Thus stannous(II)chloride, sodium dithionite or catalytic reduction may be used. In the latter case as catalyst Raney-nickel, palladium or platinum may be applied and hydrogen, hydrazine, hydrazine hydrate, formic acid, trialkyl ammonium formiate or an alkali formiate may serve as hydrogen source.

The compounds of the Formula I can be converted into pharmaceutically acceptable acid addition salts or can be set free from their salts with a stronger base. These processes can be carried out by methods known per se.

Due to their non-competitive AMPA antagonistic activity the compounds of the Formula I and pharmaceutically acceptable acid addition salts thereof exhibit among others a significant spasmolytic, muscle relaxant and neuroprotective effect and can be potentially used in case of any disease or symptom in which the inhibition of the stimulating amino acid receptors is preferred. The 2,3-benzodiazepines of the Formula I may be used in all cases wherein antagonists of the AMPA/cainate non-competitive 2,3-benzodiazepine type are effective. Thus the compounds of the Formula I can be used e.g. in the following indications: as neuroprotective agent in the treatment of symptoms accompanied by all kinds of acute or chronical neurodegeneration, e.g. Parkinsons disease, Alzheimers disease, amyotropic lateral sclerosis, stroke, acute head injuries. In addition the compounds of the Formula I can also be used to improve various symptoms, e.g. epilepsy, as spasmolytics, analgesics, as anti-emetic agents, against schizophrenia, migraine, urinating problems, as anxiolitic agents, against drug addiction and to alleviate the symptoms of Parkinsonism.

The 2,3-benzodiazepine ring of the compounds of the Formula I bear a methyl group in ortho position related to the p-amino-group of the phenyl ring. The presence of said methyl group causes an increase of effect which manifests itself in a strengthening of the effect and/or a prolongation of the duration of effect. It has been surprisingly found that in the invention compounds bearing a methyl group in ortho position acetylation of the p-amino-group in inhibited. Since N-acetylation is an important metabolic step and furthermore the N-acetyl-2,3-benzodiazepines exhibit only a weak biological effect or are even inactive, due to the inhibited acetylation inactivation of the compounds takes place more slowly and consequently the biological effect increases.

The compounds of the Formula I and salts thereof possess spasmolytic, muscle relaxant and neuroprotective effect and can be potentially used in case of any disease or symptom in which the inhibition of the stimulating amino acid receptors is preferred. The 2,3-benzodiazepines of the Formula I may be used in all cases wherein antagonists of the AMPA/cainate non-competitive 2,3-benzodiazepine type are effective. Thus the compounds of the Formula I can be used e.g. in the following indications: as neuroprotective agent in the treatment of symptoms accompanied by all kinds of acute or chronical neurodegeneration, e.g. Parkinsons disease, Alzheimers disease, amyotropic lateral sclerosis, stroke, acute head injuries. In addition the compounds of the Formula I can also be used to improve various symptoms, e.g. epilepsy, as spasmolytics, analgesics, as anti-emetic agents, against schizophrenia, migraine, urinating problems, as anxiolitic agents, against drug addiction and to alleviate the symptoms of Parkinsonism.

According to a further aspect of the present invention there are provided pharmaceutical compositions containing as active ingredient a compound of the Formula I or a pharmaceutically acceptable acid addition salt thereof.

The pharmaceutical compositions of the present invention can be administered orally (e.g. tablets, coated tablets, capsules, dragées, solutions, suspensions or emulsions), parenterally (e.g. intravenous, intramuscular or intraperitoneal injectable compositions), rectally (e.g. suppositories) or topically (e.g. ointments). The solid or liquid pharmaceutical compositions according to the invention can be prepared by methods of the pharmaceutical industry known per se.

Oral solid pharmaceutical compositions may contain binders (e.g. gelatine, sorbitol, polyvinyl pyrrolidone etc.), carriers (e.g. lactose, glucose, starch, calcium phosphate), tabletting auxiliary agents (e.g. magnesium stearate, talc, polyethylene glycol, silicic acid etc.) and wetting agents (e.g. sodium lauryl sulfate).

Oral liquid compositions may be e.g. solutions, suspensions or emulsions and may contain suspending agents (gelatine, carboxymethyl cellulose etc.), emulsifiers (e.g. sorbitan monooleate etc.), solvents (e.g. water, oils, glycerol, propylene glycol, ethanol) and stabilizing agents (e.g. methyl-p-hydroxy-benzoate).

Parenteral pharmaceutical compositions may be generally sterile solutions of the active ingredient formed with water or isotonic saline.

Rectal compositions (e.g. suppositories) contain the active ingredient dispersed in a suppository base (e.g. cocoa butter).

The pharmaceutical compositions of the invention may be prepared by methods of the pharmaceutical industry known per se. The compound of the Formula I or a pharmaceutically acceptable acid addition salt thereof is admixed with solid or liquid pharmaceutical carriers and/or auxiliary agents and brought to galenic form. The pharmaceutical composition forms and their preparation are described e.g. at Remington's Pharmaceutical Sciences, Edition 18, Mack Publishing Co., Easton, USA, (1990).

The pharmaceutical compositions according to the present invention contain generally 0.1–95% by weight of a compound of the Formula I or an acid addition salt thereof. The daily dose of the compound of the Formula I depends on various factors (e.g. efficiency of the active ingredient, age, body weight and general health of the patient, mode of administration, severeness of the disease to be treated etc.). The average daily dose is between 0.5 mg and 1000 mg for adults, preferably 20–200 mg of a compound of the Formula I. Said amount may be administered in one or more dose(s). In case of urgency a single dose of 10–1000 mg may be administered.

According to a further feature of the invention there is provided the use of compounds of the Formula I and pharmaceutically acceptable acid addition salts thereof for the preparation of pharmaceutical compositions having neuroprotective effect useful for the treatment of symptoms accompanied by all types of acute or chronical neurodegeneration (e.g. Parkinsons disease, Alzheimers disease, amyotropic lateral sclerosis, stroke, acute head injuries, epilepsy), compositions having spasmolytic, analgesic and anti-emetic effect; compositions for the treatment of schizophrenia, migraine, urination problems, against anxiety, drug addiction and to alleviate the symptoms of drug addiction and Parkinsonism.

According to a further aspect of the invention there is provided a method for the treatment of the above diseases which comprises administering to the patient in need of such treatment a pharmaceutically efficient amount of a compound of the Formula I or a pharmaceutically acceptable acid addition salt thereof.

The unexpected finding of this invention was that a methyl substitution in the ortho position to the p-amino group on the aniline moiety of 2,3-benzodiazepines resulted in a profound decrease of N-acetylation. Due to inhibited acetylation some effects of our compounds are stronger and longer lasting than those of the parent compounds in animal experiments. Decreased rate of N-acetylation can be advantageous in the human therapy since human beings can be fast or slow acetylators. Plasma level of a compound subject to N-acetylation as the main metabolic pathway can be markedly different in the fast and slow acetylator phenotypes that makes it difficult to determine the proper treatment dose of such a compound. Our unexpected finding decreases the probability of having such difficulties in the fast and slow acetylating phenotypes in the human therapy.

We use the parent compound name for the known 2,3-benzodiazepines without ortho-methyl substitution.

Effect of the Ortho Substitution on the Rate of N-Acetylation

Method

Liver slices of (WI) BR rats were incubated in oxigenized Krebs-Ringer solution at 37° C. in the presence of 50 μM 2,3-benzodiazepines (Compound A–F). 0.5 ml aliquots were obtained from the incubation mixture after 0, 30 and 60 min.

2,3-benzodiazepines were chosen as internal standards for the experiments according to the retention times of the compounds measured. Plasma proteins were precipitated with perchloric acid and 2,3-benzodiazepines were extracted with chloroform after alkalization. After evaporation to dryness the residue was dissolved in eluent.

Beckman System Gold HPLC was used with a C-18 reversed-phase column and an UV detector at 240 nm. Different eluents were used for the optimal separation of the compounds:

Eluent A: 50% 2 mM heptafluorobutyric acid, 35% methanol, 15% acetonitrile.

Eluent B: 55% 2 mM heptafluorobutyric acid, 25% methanol, 20% acetonitrile.

Eluent C: 50% 2 mM heptafluorobutyric acid, 40% methanol, 10% acetonitrile.

The percentage of N-acetyl metabolite content of the samples at a certain time was calculated as follows: the peak area of the metabolite was divided with the sum of the peak areas of the compound and the metabolite.

$$\text{N-ac. met. } (\%)_t = \frac{100 \text{ N-ac. met. } PA_t}{\text{N-ac. met. } PA_t + \text{Compound } PA_t}$$

$t^2$: time (30 or 60 min)

N-ac. met.: N-acetyl metabolite

PA: Peak Area

Results

Figure 2:
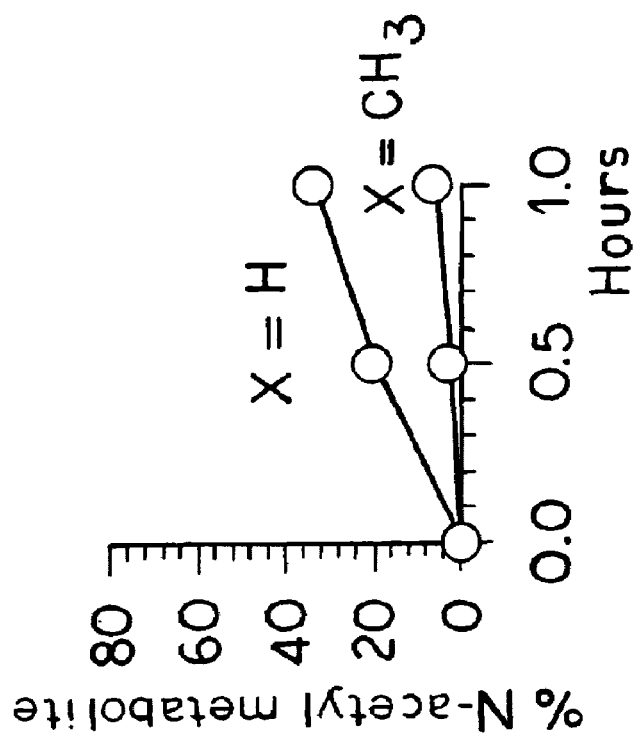
FIG. 2 is a set of graphs comparing the percentages of formation of the N-acetyl metabolites of Compound B with and without a methyl group ortho to the amino group (X=H prior art, X=CH₃ present invention, respectively) over a period of one hour in liver slices of WI BR rats incubated in oxygenated Krebs-Ringer solution at 37° C.
Figure 1:
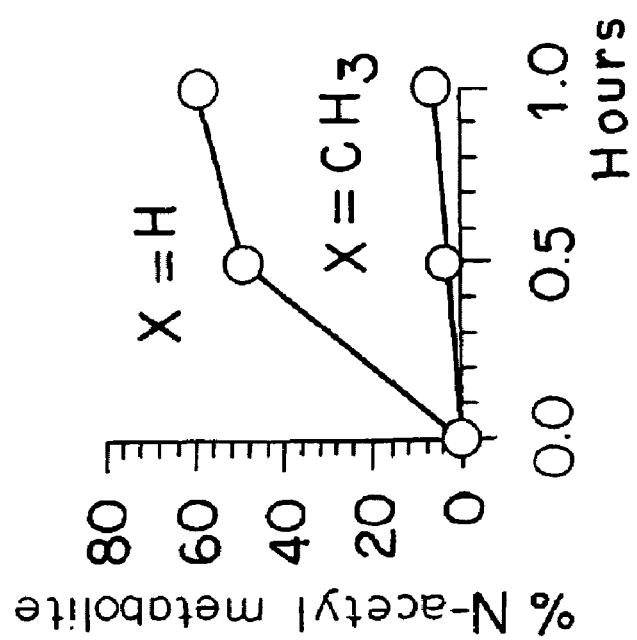
FIG. 1 is a set of graphs comparing the percentages of formation of the N-acetyl metabolites of C A with and without a methyl group ortho to the amino group (X=H prior art, X=CH₃ present invention, respectively) over a period of one hour in liver slices of WI BR rats incubated in oxygenated Krebs-Ringer solution at 37° C.
Figure 4:
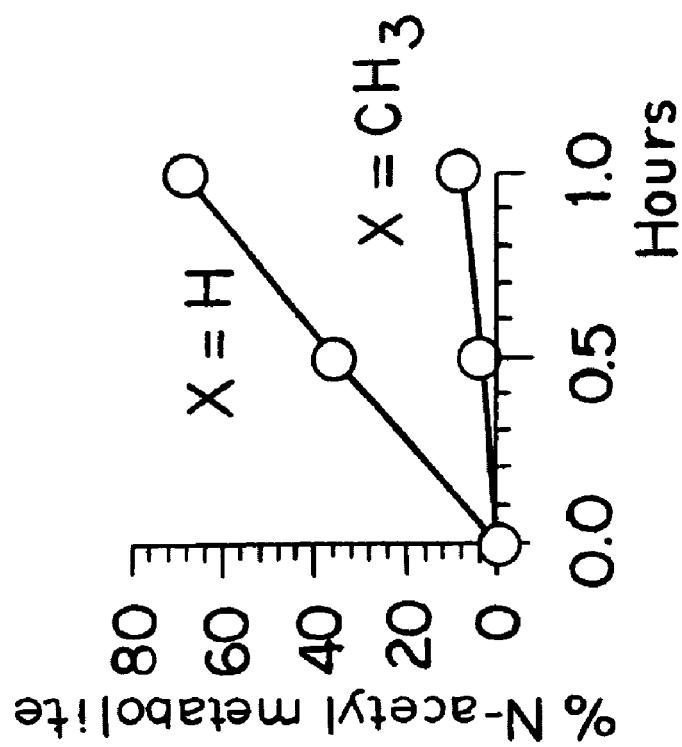
FIG. 4 is a set of graphs comparing the percentages of formation of the N-acetyl metabolites of Compound D with and without a methyl group ortho to the amino group (X=H prior art, X=CH₃ present invention, respectively) over a period of one hour in liver slices of WI BR rats incubated in oxygenated Krebs-Ringer solution at 37° C.
Figure 3:
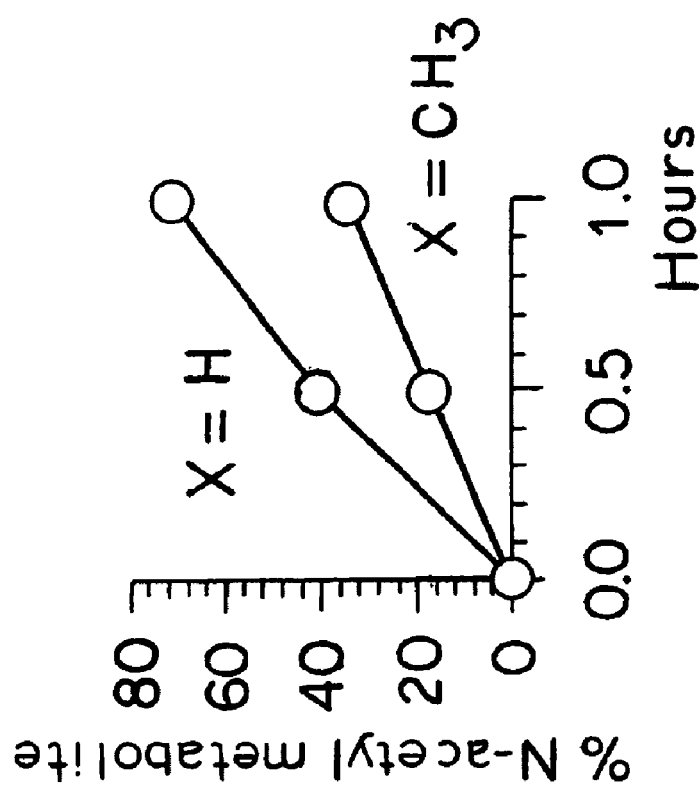
FIG. 3 is a set of graphs comparing the percentages of formation of the N-acetyl metabolites of Compound C with and without a methyl group ortho to the amino group (X=H prior art, X=CH₃ present invention, respectively) over a period of one hour in liver slices of WI BR rats incubated in oxygenated Krebs-Ringer solution at 37° C.
Figure 6:
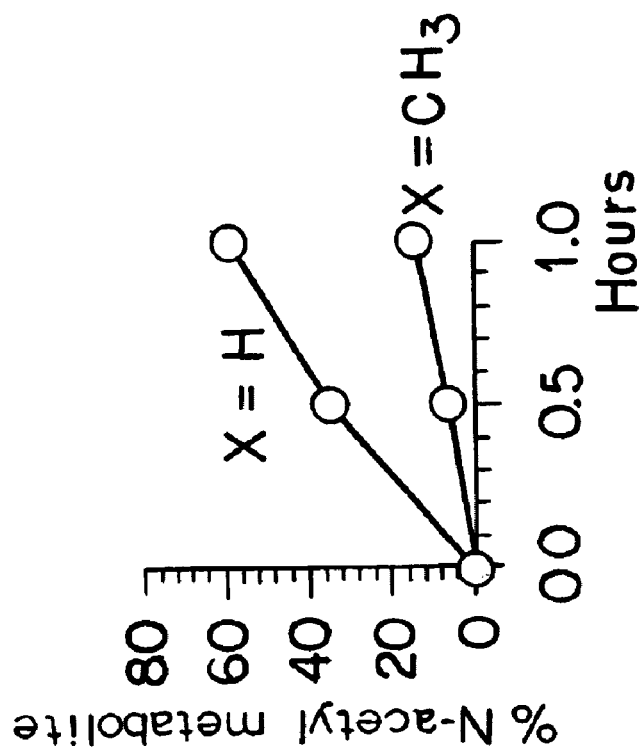
FIG. 6 is a set of graphs comparing the percentages of formation of the N-acetyl metabolites of Compound F with and without a methyl group ortho to the amino group (X=H prior art, X=CH₃ present invention, respectively) over a period of one hour in liver slices of WI BR rats incubated in oxygenated Krebs-Ringer solution at 37° C.
Figure 5:
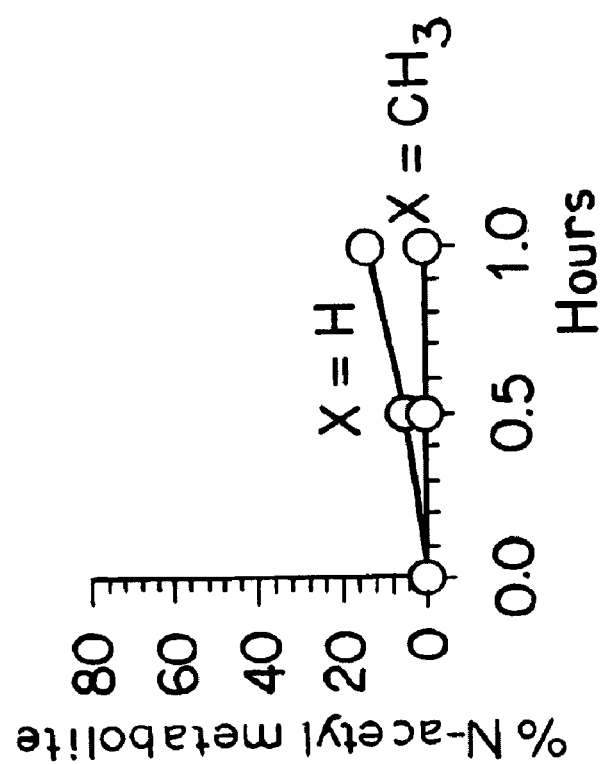
FIG. 5 is a set of graphs comparing the percentages of formation of the N-acetyl metabolites of Compound E with and without a methyl group ortho to the amino group (X=H prior art, X=CH₃ present invention, respectively) over a period of one hour in liver slices of WI BR rats incubated in oxygenated Krebs-Ringer solution at 37° C.

The next figures show that N-acetylation is always slower in the case of the o-methylated compounds than in the case of the parent ones, i.e. o-methylation inhibits the N-acetylation. Compound A X=H X=CH₂

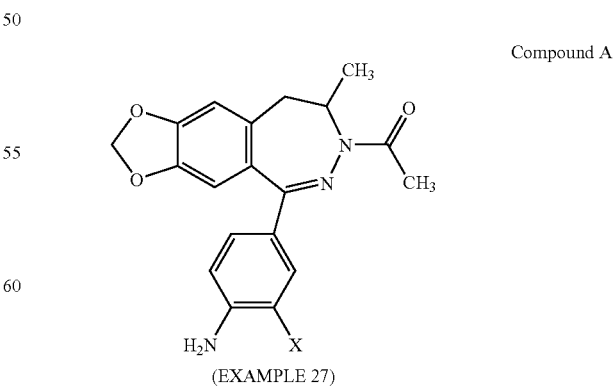

Compound A (EXAMPLE 27)

X = H
X = CH₃

Compound B

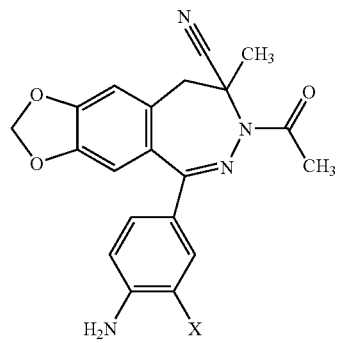

X = H
X = CH₃

Compound C

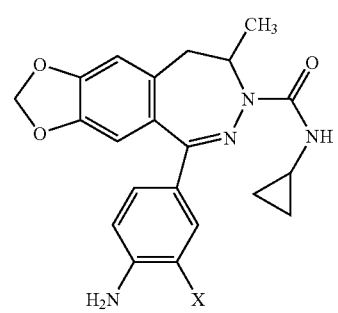

(Example 29)

X = H
X = CH₃

Compound D

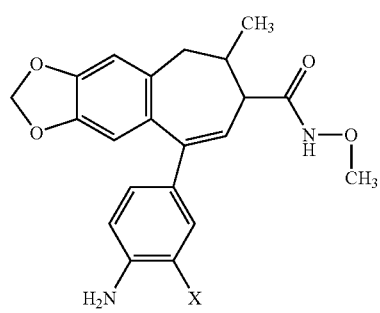

(Example 30)

X = H
X = CH₃

Compound B

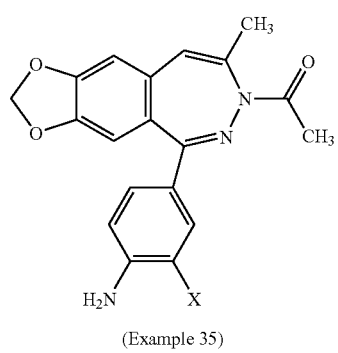

(Example 35)

X = H
X = CH₃

Compound P

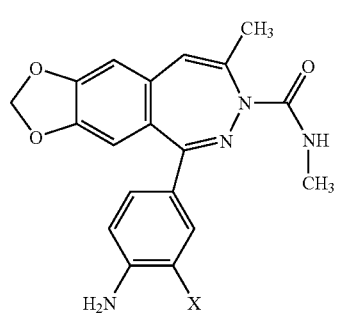

(Example 36)

X = H
X = CH₃

Neuroprotective Effect in MgCl2-Induced Global Cerebral Ischemia in Mice

Method

Male NMRI mice weighing 20–25 g were randomly allocated to treatment groups of 10 animals/group. The compounds were dissolved in 5 M hydrochloric acid solution and distilled water (5%/95% v/v) then the pH of the solution was adjusted to 3 using 1 M sodium hydroxide solution. The compounds were administered intraperitoneally in a volume of 10 ml/kg. Each compound was tested at four increasing dose levels and a separate group of animals was treated with the vehicle. Thirty min after treatment all mice received an intravenous bolus injection of saturated $MgCl_2$ solution (5 ml/kg) that caused an immediate cardiac arrest and complete cerebral ischemia. Increases in survival time (interval between the injection of $MgCl_2$ and the last observable gasp) were used as a measure of neuroprotective effect as described by Berga et al. [1]. Percentage changes in survival time were calculated in comparison to that measured in the vehicle treated group. $PD_{50}$ (the dose that prolonged survival by 50%) was calculated by linear regression analysis using percentage changes in survival time.

Results

The table shows the effects of compounds on survival time in mice in comparison to their parent compounds.

| Test compound Example No. | X = H PD$_{50}$, mg/kg i.p. | X = CH$_3$ PD$_{50}$, mg/kg i.p. |
|---|---|---|
| Compound A Example 27 | 8.3 | 5.4 |
| Compound B Example 38 | 18.7 | 11.2 |
| Compound D Example 30 | 27.4 | 14.9 |

PD$_{50}$ of all three o-substituted derivatives of the table was lower than that of their parent compounds. This means that o-methylation increased the neuroprotective effect of the compounds.

Reference

1. Berga, P., Beckett, P. R., Roberts, D. J., Llenas, J., Massingham, R.: Synergistic interactions between piracetam and dihydroergocristine in some animal models of cerebral hypoxia and ischaemia., Arzneim.-Forsch. 36, 1314–1320 (1986).

Duration of Action in Rats as Assessed from the Decrease in Body Core Temperature Method At least one week prior to treatments six male Wistar rats were anaesthetised with pentobarbital-Na (60 mg/kg, i.p.; Nembutal, Phylaxia-Sanofi, Budapest). Using sterile surgical procedures TL11M2-C50-PXT or TA10TA-F40 type radiotelemetry transmitters (Data Sciences International, St. Paul, Minn., USA) permitting continuous monitoring of core body temperature were implanted into the peritoneal cavity of the animals. After surgery the rats were treated with an antibiotic (1 ml/kg b.w. i.m. Tardomyocel, Bayer A G, Leverkusen, Germany). The animals were housed individually in type 2 plastic rat cages with free access to food and tap water. The compounds were dissolved in 5 M hydrochloric acid solution and distilled water (5%/95% v/v) then the pH of the solution was adjusted to 3 using 1 M sodium hydroxide solution. The compounds were administered intraperitoneally in a volume of 10 ml/kg.

Radio signals emitted by the transmitters were detected by RLA1000 type receivers placed under each animal's cage. Data were collected and saved by a Dataquest IV computerised data acquisition system. The computer was set to sample body temperature for 10 seconds in every second minute. Mean values for 30 min periods over the whole day were calculated running the "Sort Utility" of the Dataquest IV. System. The upper and lower limits of the evaluating routine were set to exclude biologically improbable values. Individual body temperature curves were averaged for the six animals.

Peak effect (PE) was measured as the maximum decrease in body temperature in comparison to the last value prior to treatment. Using mean values, duration of action (D) was measured as the time interval from treatment to return of body temperature to the control level.

Results

The table shows the peak effect (PE) of different o-substituted derivatives on body temperature in rats in comparison to their parent compounds.

| Test compound Example No. | X = H PE, Δ ° C. | X = CH$_3$ PE, Δ ° C. |
|---|---|---|
| Compound A Example 27 | −1.26 | −1.45 |
| Compound B Example 38 | −0.93 | −1.34 |
| Compound G Example 31 | −1.12 | −1.46 |

Compound G:

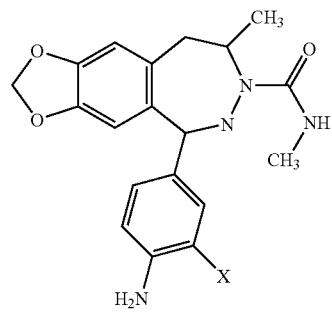

The table shows the duration of action (D) of different o-substituted derivatives on body temperature in rats in comparison to their parent compounds.

| Test compound Example No. | X = H D, hours | X = CH$_3$ D, hours |
|---|---|---|
| Compound A Example 27 | 5 | >20 |
| Compound B Example 38 | 6 | 9 |
| Compound G Example 31 | 5 | 20 |

The maximum decrease in body temperature was larger and the duration of action was longer for the different o-substituted derivatives in comparison to their parent compounds. This means that the o-methylation results in a stronger and longer lasting effect then its parent compound.

Further details of the present invention are to be found in the following Examples without limiting the scope of protection to said Examples.

EXAMPLE 1

(±)-3-methyl-1-(3-methyl-4-nitro-phenyl)-1,3-dioxolo[4,5-g]isochromane

To a solution of 3.30 g (20.0 millimoles) of 3-methyl-4-nitro-benzaldehyde and 3.60 g (20.0 millimoles) of (±)-5-(2-hydroxy-1-propyl)-1,3-dioxolo[4,5-a]benzene in 40 ml of toluene 3.0 ml of concentrated hydrochloric acid are added. The reaction mixture is stirred at room temperature for a day, whereupon the mixture is diluted with 60 ml of toluene, washed with 40 ml of water, 20 ml of a concentrated sodium carbonate solution and 20 ml of a saturated sodium chloride solution, dried over magnesium sulfate and evaporated in vacuo. The crude product obtained is recrystallized from 80 ml of ethanol. Thus 4.59 g of the desired compound are obtained, yield 76%, mp.: 122–123° C.

$C_{18}H_{17}NO_5$ (327.34) $^1$H NMR (CDCl$_3$) δ 7.96 (1H, d, J=8.8 Hz), 7.32 (2H, s), 6.60 (1H, s), 6.07 (1H, s), 5.87 (1H, d, J=1.2 Hz), 5.85 (1H, d, J=1.2 Hz), 5.66 (1H, s), 4.95 (1H, m), 2.75 (2H, m), 2.60 (3H, s), 1.38 (3H, d, J=6.0 Hz).

EXAMPLE 2

5-(3-methyl-4-nitro-benzoyl)-6-(2-oxo-1-propyl)-1, 3-dioxolo[4,5-a]benzene 3.28 g (10.0 millimoles) of (±)-3-methyl-1-(3-methyl-4-nitro-phenyl)-1,3-dioxolo[4,5-g]isochromane are dissolved in 60 ml of acetone, whereupon 10 ml of a Jones reagent containing 2.60 g (26.0 millimoles) of CrO$_3$ and 2.15 ml of concentrated sulfuric acid are added dropwise under cooling with icecold water. The reaction mixture is stirred at room temperature for a day, whereupon the acetone is decanted and the residue is evaporated. The evaporation residue and the unsoluble part of the reaction mixture are taken up in a mixture of 75 ml of dichloro methane and 75 ml of water. The phases are separated and the aqueous layer is extracted twice with 50 ml of dichloro methane each. The united organic phases are washed with 50 ml of water, 50 ml of a saturated sodium chloride solution, dried over magnesium sulfate and evaporated in vacuo. The crude product obtained is crystallized from 50 ml of ethanol. Thus 2.15 g of the desired compound are obtained, yield 62%, mp.: 146–148° C.

$C_{19}H_{15}NO_6$ (341.32) $^1$H NMR (CDCl$_3$) δ 7.97 (1H, d, J=8.3 Hz), 7.70 (1H, s), 7.66 (1H, d, J=8.4 Hz), 6.82 (1H, s), 6.74 (1H, s), 6.04 (2H, s), 3.97 (2H, s), 2.61 (3H, s), 2.22 (3H, s).

EXAMPLE 3

3-methyl-1-(3-methyl-4-nitro-phenyl)-1,3-dioxolo[4, 5-g]benzpyrilium-perchlorate 1.73 g (5.07 millimoles) of 4-(3-methyl-4-nitro-benzoyl)-5-(2-oxo-1-propyl)-1,3-dioxolo[4,5-a]-benzene are dissolved in 50 ml of ethyl acetate, whereupon 0.85 g (0.51 ml, 5.93 millimoles) of 70% perchloric acid are added and the reaction mixture is stirred under boiling for an hour and thereafter cooled to 4° C. by cooling with ice-cold water. The precipitated product is filtered and washed with 10 ml of cold ethyl acetate. Thus 2.08 g of the desired compound are obtained, yield 97%, mp.: 262–266° C.

$C_{18}H_{14}ClNO_9$ (423.77)

EXAMPLE 4

8-methyl-5-(3-methyl-4-nitro-phenyl)-9H-1,3-dioxolo[4.5-h][2,3]benzodiazepine 1.90 g (4.48 millimoles) of 3-methyl-1-(3-methyl-4-nitro-phenyl)-1,3-dioxolo[4,5-g]benzpyrilium-perchlorate are suspended in 35 ml of methanol, whereupon 1.31 g (1.30 ml, 26.23 millimoles) of 100% hydrazine hydrate are added and the reaction mixture is stirred at room temperature for a day. The mixture is evaporated in vacuo and the residue is taken up in 50 ml of dichloro methane. The organic solution is washed three times with ml of water each, drived over magnesium sulfate and evaporated in vacuo. The crude product obtained is recrystallized from 15 ml of ethanol. Thus 1.20 g of the desired compound are obtained, yield 79%, mp.: 189–194° C.

$C_{18}H_{15}N_3O_4$ (337.34) $^1$H NMR (CDCl$_3$) δ 7.98 (1H, d, J=8.5 Hz), 7.74 (1H, s), 7.58 (1H, dd, J=8.5 and J=1.5 Hz), 6.78 (1H, s), 6.67 (1H, s), 6.07 (1H, s), 6.01 (1H, s), 3.30 (1H, d, J=12.3 Hz), 2.91 (1H, d, J=12.3 Hz), 2.63 (3H, s), 2.16 (3H, s).

EXAMPLE 5

(±)-7,8-dihydro-8-methyl-5-(3-methyl-4-nitro-phenyl)-9H-1,3-dioxolo[4.5-h][2.3]benzodiazepine 1.69 g (10.0 millimoles) of 8-methyl-5-(3-methyl-4-nitro-phenyl)-9H-1,3-dioxolo[4,5-h][2,3]benzodiazepine are dissolved in a mixture of 75 ml of dichloro methane, 5 ml of methanol and 3 ml of glacial acetic acid. To the reaction mixture 0.38 g (10.0 millimoles) of sodium borohydride are added under cooling with ice-cold water in small portions. The reaction mixture is stirred at this temperature for an hour, then washed twice with 20 ml of water and 20 ml of saturated sodium chloride solution each, washed over magnesium sulfate and evaporated in vacuo. The crude product obtained is recrystallized from 50 ml of acetonitrile each. Thus 1.20 g of the desired compound are obtained, yield 71%, mp.: 124–127° C.

$C_{19}H_{17}N_3O_4$ (339.35) $^1$H NMR (CDCl$_3$) δ 7.96 (1H, d, J=8.4 Hz), 7.52 (1H, s), 7.46 (1H, dd, J=8.4 and J=1.5 Hz), 6.74 (1H, s), 6.50 (1H, s), 5.98 (2H, s), 5.58 (1H, broad s), 4.09 (1H, m), 2.87 (1H, dd, J=13.9 and J=4.0 Hz), 2.62 (1H, dd, J=13.6 and J=6.6 Hz), 2.61 (3H, s), 1.27 (3H, d, J=6.2 Hz).

EXAMPLE 6

(±)-7-acetyl-7,8-dihydro-8-methyl-5-(3-methyl-4-nitro-phenyl)-9H-1,3-dioxolo[4,5-h][2,3]benzodiazepine 1.70 g (5.0 millimoles) of (±)-7,8-dihydro-8-methyl-5-(3-methyl-4-nitro-phenyl)-9H-1,3-dioxolo[4,5-h][2,3]benzodiazepine are stirred in 10 ml of acetic anhydride at room temperature for a day. The reaction mixture is poured into a mixture of 100 ml of water and 75 ml of dichloro methane, stirred for an hour and the pH is adjusted to 8 by adding sodium carbonate in portions. The layers are separated, the aqueous phase is extracted twice with 25 ml of dichloro methane each. The united organic phases are washed with 50 ml of saturated sodium chloride solution, dried over magnesium sulfate and evaporated. The crude product obtained is recrystallized from 15 ml of ethanol. Thus 1.65 g of the desired product are obtained, yield 87%, mp.: 178–181° C.

$C_{20}H_{19}N_3O_5$ (381.39) $^1$H NMR (CDCl$_3$) δ 8.04 (1H, d, J=9.2 Hz), 7.50 (2H, m), 6.76 (1H, s), 6.49 (1H, s), 6.02 (2H, s), 5.38 (1H,m), 3.01 (1H, dd, J=13.6 and J=3.3 Hz), 2.76 (1H, dd, J=13.6 and J=8.4 Hz), 2.64 (3H, s), 2.29 (3H, s), 1.08 (3H, d, J=6.6 Hz).

EXAMPLE 7

(±)-7,8-dihydro-8-methyl-5-(3-methyl-4-nitro-phenyl)-7-propionyl-9H-1,3-dioxolo[4,5-h][2,3] benzodiazepine 1.70 g (5.0 millimoles) of (±)-7,8-dihydro-8-methyl-5-(3-methyl-4-nitro-phenyl)-9H-1,3-dioxolo[4,5-h][2,3]benzodiazepine are stirred in 10 ml of propionic anhydride at room temperature for a day. The reaction mixture is poured into a mixture of 100 ml of water and 75 ml of dichloro methane, stirred for an hour and the pH is adjusted to 8 by adding sodium carbonate in portions. The phases are separated, the aqueous layer is extracted twice with 25 ml of dichloro methane each. The united organic layers are washed with 50 ml of a saturated sodium chloride solution, dried over magnesium sulfate and evaporated. The crude product obtained is recrystallized from 35 ml of diethyl ether. Thus 1.40 g of the desired product are obtained, yield 71%, mp.: 172–175° C.

$C_{21}H_{21}N_3O_5$ (395.42) $^1$H NMR (CDCl$_3$) δ 8.00 (1H, d, J=9.6 Hz), 7.54 (2H, m), 6.77 (1H, s), 6.49 (1H, s), 6.01 (2H, s), 5.37 (1H,m), 2.98 (1H, dd, J=14.5 and J=3.4 Hz), 2.76 (1H, dd, J=14.6 and J=8.7 Hz), 2.66 (2H, m), 2.64 (3H, s), 1.14 (3H, t, J=7.4 Hz), 1.09 (3H, d, J=6.5 Hz).

EXAMPLE 8

(±)-7,8-dihydro-8-methyl-5-(3-methyl-4-nitro-phenyl)-9H-1,3-dioxolo[4,5-h][2,3]benzodiazepine-7-carboxylic acid-imidazolide A mixture of 3.37 g (10.0 millimoles) of (±)-7,8-dihydro-8-methyl-5-(3-methyl-4-nitro-phenyl)-9H-1,3-dioxolo[4,5-h][2,3]benzodiazepine, 1.95 g (12.0 millimoles) of 1,1'-carbonyl-diimidazole and 75 ml of anhydrous tetrahydrofurane is stirred under boiling for 20 hours. The reaction mixture is cooled with icecold water. The precipitated product is filtered and washed with 50 ml of diethyl ether. Thus 3.55 g of the desired product are obtained, yield 82%, mp.: 223–226° C.

$C_{22}H_{19}N_5O_5$ (433.43) $^1$H NMR ((CD$_3$)$_2$SO) δ 8.06 (1H, d, J=8.5 Hz), 7.96 (1H, s), 7.57 (1H, s), 7.54 (1H, dd, J=8.5 Hz and J=1.5 Hz), 7.38 (1H, s), 7.04 (1H, s), 7.13 (1H, s), 6.87 (1H, s), 6.13 (1H, d, J=0.8 Hz), 6.10 (1H, d, J=0.9 Hz), 5.08 (1H, m), 3.30 (3H, s), 3.05 (1H, dd, J=14.3 and J=5.0 Hz), 2.73 (1H, dd, J=14.2 and 10.2 Hz), 1.30 (3H, d, J=6.2 Hz).

EXAMPLE 9

(±)-7-(N-cyclopropyl-carbamoyl)-7,8-dihydro-8-methyl-5-(3-methyl-4-nitro-phenyl)-9H-1,3-dioxolo[4.5-h]-[2.3]benzodiazepine 4.33 g (10.0 millimoles) of (±)-7,8-dihydro-8-methyl-5-(3-methyl-4-nitro-phenyl)-9H-1,3-dioxolo[4,5-h][2,3]benzodiazepine-7-carboxylic acid-imidazolide are heated to boiling in 30 ml of cyclopropyl amine for 6 hours, whereupon the amine is distilled off in vacuo. The residue is taken up in 75 ml of dichloro methane, washed three times with 30 ml of water each, dried over magnesium sulfate and evaporated in vacuo. The crude product obtained is recrystallized from 40 ml of ethanol and washed with 10 ml of diethyl ether. Thus 3.00 g of the desired product are obtained, yield 71%, mp.: 171–175° C.

$C_{22}H_{22}N_4O_5$ (422.44) $^1$H NMR (CDCl$_3$) δ 8.01 (1H, d, J=8.4 Hz), 7.41 (2H, m), 6.71 (2H, s), 6.45 (1H, s), 6.00 (1H, s), 5.99 (1H, s), 5.48 (1H, m), 3.10 (1H, m), 2.85 (1H, dd, J=14.5 and 7.2 Hz), 2.68 (1H, m), 2.63 (3H, s), 0.95 (3H, d, J=6.6 Hz), 0.77 (2H, m), 0.54 (2H, m).

EXAMPLE 10

(±)-7.8-dihydro-8-methyl-5-(3-methyl-4-nitro-phenyl)-7-(N-methoxy-carbamoyl)-9H-1,3-dioxolo[4,5-h][2,3]benzodiazepine 2.03 g (25.0 millimoles) of methoxy-amine hydro-chloride and 3.45 g (25.0 millimoles) of potassium carbonate are stirred in 75 ml of anhydrous dimethyl formamide for half an hour whereupon 2.17 g (5.0 millimoles) of (±)-7,8-dihydro-8-methyl-5-(3-methyl-4-nitro-phenyl)-9H-1,3-dioxolo[4,5-h][2,3]benzodiazepine-7-carboxylic acid-imidazolide are added. The reaction mixture is stirred for 16 hours, whereupon the solvent is evaporated at a pressure of 55 Pa. The residue is suspended in 100 ml of water, stirred for half an hour, washed with 50 ml of water and dried. The crude product is recrystallized from 30 ml of acetonitrile and washed with 10 ml of diethyl ether. Thus 1.59 g of the desired compound are obtained, yield 77%, mp.: 192–195° C.

$C_{20}H_{20}N_4O_6$ (412.41) $^1$H NMR (CDCl$_3$) δ 8.90 (1H, s), 8.00 (1H, d, J=9.2 Hz), 7.41 (2H, m), 6.73 (1H, s), 6.45 (1H, s), 6.01 (1H, m), 5.35 (1H, m), 3.81 (3H, s), 3.12 (1H, dd, J=14.7 and J=2.2 Hz), 2.85 (1H, dd, J=14.7 and J=6.6 Hz), 2.64 (3H, s), 1.00 (3H, d, J=6.6 Hz).

EXAMPLE 11

(±)-7,8-dihydro-8-methyl-7-(N-methyl-carbamoyl)-5-(3-methyl-4-nitro-phenyl)-9H-1,3-dioxolo[4,5-h][2.3]benzodiazepine A mixture of 2.17 g (5.0 millimoles) of (±)-7,8-dihydro-8-methyl-5-(3-methyl-4-nitro-phenyl)-9H-1,3dioxolo[4,5-h][2,3]benzodiazepine-7-carboxylic acid-imidazolide, 75 ml of dichloro methane and 15 ml of a 33% ethanolic methyl amine solution is stirred for 3 hours. The reaction mixture is evaporated in vacuo and the residue is suspended in 75 ml of water. The crude product is filtered off, washed with 25 ml of water, dried and recrystallized from 25 ml of ethanol. Thus 1.68 g of the desired compound are obtained, yield 85%, mp.: 221–229° C.

$C_{20}H_{20}N_4O_5$ (396.41) $^1$H NMR (CDCl$_3$) δ 8.00 (1H, d, J=9.2 Hz), 7.40 (2H, m), 6.72 (1H, s), 6.53 (1H, m), 6.46 (1H, s), 6.01 (1H, s), 6.00 (1H, s), 5.463 (1H, m), 3.11 (1H, m), 2.89 (4H, m), 2.64 (3H, s), 0.95 (3H, d, J=6.6 Hz).

EXAMPLE 12

8-formyl-5-(3-methyl-4-nitro-phenyl)-9H-1,3-dioxolo[4,5-h][2,3]benzodiazepine

A mixture of 3.37 g (10.0 millimoles) of 8-methyl-5-(4-nitro-3-methyl-phenyl)-9H-1,3-dioxolo[4,5-h][2,3]benzodiazepine, 1.66 g (10.5 millimoles) of selen(IV)oxide and 100 ml of dioxane is stirred on an oil-bath at 80° C. for 3 hours. The solution is filtered on a hot coal-bed washed with 50 ml of hot dioxane and evaporated in vacuo. The crude product obtained is treated with 20 ml of acetonitrile. Thus 2.42 g of the desired compound are obtained, yield 69%, mp.: 188–191° C.

$C_{18}H_{13}N_3O_5$ (337.29) $^1$H NMR (CDCl$_3$) δ 9.54 (1H, s), 8.02 (1H, d, J=8.4 Hz), 7.79 (1H, s), 7.65 (1H, dd, J=8.4 Hz and J=1.8 Hz), 6.82 (1H, s), 6.61 (1H, s), 6.15 (1H, d, J=07 Hz), 6.03 (1H, d, J=1.1 Hz), 4.11 (1H, d, J=12.8 Hz), 2.62 (1H, d, J=12.1 Hz), 2.66 (3H, s)

EXAMPLE 13

5-(3-methyl-4-nitro-phenyl)-9H-1,3-dioxolo[4.5-h][2,3]benzodiazepine-8-carboxylic acid To a solution of 3.40 g (20.0 millimoles) of silver(I)nitrate and 25 ml of water a solution of 1.60 g (4.0 millimoles) of sodium hydroxide and 25 ml of water is added. The mixture is stirred for 10 minutes, diluted with 50 ml of tetrahydrofurane and 3.51 g (10.0 millimoles) of 8-formyl-5-(3-methyl-4-nitro-phenyl)-9H-1,3-dioxolo[4,5-h][2,3]benzodiazepine are added under cooling with icecold water. The reaction mixture is stirred at room temperature for 5 hours, filtered on a coal-bed and washed with cold water. The pH of the solution is adjusted to 2 with 6 N hydrochloric acid. After cooling the precipitated product is filtered and washed with 10 ml of cold water. Thus 2.61 g of the desired compound are obtained, yield 71%, mp.: 185–186° C.

$C_{18}H_{13}N_3O_6$ (367.32) $^1$H NMR ((CD$_3$)$_2$SO) δ 13.40 (1H, broad s), 8.08 (1H, d, J=8.8 Hz), 7.74 (1H, s), 7.63 (1H, dd, J=8.3 Hz and J=1.5 Hz), 7.05 (1H, s), 6.83 (1H, s), 6.17 (1H, s), 6.10 (1H, s), 4.08 (1H, d, J=12.7 Hz), 2.75 (1H, d, J=12.7 Hz), 2.57 (3H, s).

EXAMPLE 14

5-(3-methyl-4-nitro-phenyl)-9H-1,3-dioxolo[4.5-h]-[2,3]benzodiazepine-8-carboxylic acid-imidazolide 3.67 g (10.0 millimoles) of 5-(3-methyl-4-nitro-phenyl)-9H-1,3-dioxolo[4,5-h][2,3]benzodiazepine-8-carboxylic acid are suspended in 75 ml of anhydrous dimethyl-formamide and 1.95 g (12.0 millimoles) of 1,1'-carbonyl-diimidazole are added in one portion. The reaction mixture is stirred at room temperature for 5 hours and cooled with icecold water. The precipitated product is filtered and washed with 50 ml of diethyl ether. Thus 3.21 g of the desired compound are obtained, yield 77%, mp.: 132–136° C.

$C_{21}H_{15}N_5O_5$ (417.38) $^1$H NMR ((CD$_3$)$_2$SO) δ 8.53 (1H, s), 8.08 (1H, d, J=9.2 Hz), 7.81 (1H, S), 7.80 (1H, s), 7.66 (1H, d, J=8.3 Hz), 7.16 (1H, s), 7.10 (1H, s), 6.84 (1H, s), 6.18 (1H, s), 6.11 (1H, s), 4.17 (1H, d, J=13.6 Hz), 2.83 (1H, d, J=13.4 Hz), 2.58 (3H, s).

EXAMPLE 15

5-(3-methyl-4-nitro-phenyl)-9H-1,3-dioxolo[4.5-h][2,3]benzodiazepine-8-carboxylic acid-amide 4.17 g (10.0 millimoles) of 5-(3-methyl-4-nitro-phenyl)-9H-1,3-dioxolo[4,5-h][2,3]benzodiazepine-8-carboxylic acid-imidazolide are suspended in a mixture of 85 ml dichloro methane and 15 ml of a 15% aqueous methanolic ammonia solution. The reaction mixture is sealed and stirred at room temperature for 6 hours. The mixture is cooled with icecold water. The precipitated product is filtered and washed with 20 ml of diethyl ether. Thus 3.11 g of the desired compound are obtained, yield 85%, mp.: 266–268° C.

$C_{18}H_{14}N_4O_5$ (366.34) $^1$H NMR ((CD$_3$)$_2$SO) δ 8.08 (1H, d, J=8.4 Hz), 7.82 (1H, broad s), 7.73 (1H, broad s), 7.61 (2H, m), 7.01 (1H, s), 6.80 (1H, s), 6.16 (1H, s), 6.09 (1H, s), 4.23 (1H, d, J=12.5 Hz), 3.37 (3H, s), 2.64 (1H, d, J=12.5 Hz).

EXAMPLE 16

(±)-7.8-dihydro-5-(3-methyl-4-nitro-phenyl)-9H-1,3-dioxolo[4,5-h][2,3]benzodiazepine-8-carboxylic acid-amide 1.76 g (5.0 millimoles) of 5-(3-methyl-4-nitro-phenyl)-9H-1,3-dioxolo[4,5-h][2,3]benzodiazepine-8-carboxylic acid-amide are suspended in a mixture of 75 ml ethanol and 75 ml of dichloro methane, whereupon 0.19 g (5.0 millimoles) of sodium-[tetrahydrido-borate(IV)] are added in one portion and a solution of 0.55 g (5.0 millimoles) of calcium chloride in 25 ml of ethanol is added dropwise. The reaction mixture is stirred at room temperature for 25 hours and evaporated in vacuo. The residue is heated to boiling in 100 ml of water for half an hour and filtered hot. The crude product obtained is heated to boiling in 50 ml of acetonitrile for half an hour, cooled with icecold water, filtered and washed with 20 ml of diethyl ether. Thus 1.27 g of the desired compound are obtained, yield 69%, mp.: 246–249° C.

$C_{18}H_{16}N_4O_5$ (368.35) $^1$H NMR ((CD$_3$)$_2$SO) δ 7.98 (1H, d, J=8.8 Hz), 7.72 (1H, d, J=5.1 Hz), 7.49 (1H, broad s), 7.41 (1H, d, J=8.1 Hz), 7.21 (2H, broad s), 6.82 (1H, s), 6.47 (1H, s), 6.03 (2H, s), 4.30 (1H, m), 3.35 (3H, s), 2.99 (2H, m).

EXAMPLE 17

(±)-7-acetyl-7,8-dihydro-5-(3-methyl-4-nitro-phenyl)-9H-1,3-dioxolo[4,5-h][2,3]benzodiazepine-8-carboxylic acid-amide 3.68 g (10.0 millimoles) of (±)-7,8-dihydro-5-(3-methyl-4-nitro-phenyl)-9H-1,3-dioxolo[4,5-h][2,3]benzodiazepine-8-carboxylic acid-amide are suspended in 30 ml of acetic anhydride and stirred at room temperature for 48 hours. The reaction mixture is cooled with icecold water, the precipitated product is filtered and washed with 20 ml of diethyl ether. Thus 3.32 g of the desired compound are obtained, yield 81%, mp.: 157–161° C.

$C_{20}H_{18}N_4O_6$ (410.39) $^1$H NMR ((CD$_3$)$_2$SO) δ 8.05 (1H, d, J=8.1 Hz), 7.56 (2H, m), 7.27 (1H, broad s), 6.97 (1H, broad s), 6.87 (1H, s), 6.49 (1H, s), 6.07 (2H, s), 5.45 (1H, m), 3.18 (2H, m), 2.32 (3H, s), 2.22 (3H, s).

EXAMPLE 18

8-cyano-5-(3-methyl-4-nitro-phenyl)-9H-1,3-dioxolo[4,5-h][2,3]benzodiazepine

A mixture of 3.51 g (10.0 millimoles) of 8-formyl-5-(3-methyl-4-nitro-phenyl)-9H-1,3-dioxolo[4,5-h][2,3]benzodiazepine, 0.83 g (12.0 millimoles) of hydroxy-amine hydrochloride and 1.09 g (13.0 millimoles) of anhydrous sodium acetate and 100 ml of ethanol is stirred under boiling for 10 hours, whereupon the reaction mixture is evaporated in vacuo. The residue is suspended in 150 ml of water, stirred at room temperature for half an hour, filtered and washed with 25 ml of water. The oxime thus obtained is dried, suspended in 100 ml of dichloro-methane, 2.42 g (3.34 ml, 24.0 millimoles) of triethyl amine are added and a solution of 1.32 g (0.93 ml, 12.0 millimoles of methane-sulfonyl chloride in 1.0 ml of dichloro methane is added dropwise under cooling with icecold water. The reaction mixture is stirred at room temperature for 4 hours, washed twice with 30 ml of water and 30 ml of a saturated sodium chloride solution each, drived over magnesium sulfate and evaporated in vacuo. The crude product thus obtained is recrystallized from 55 ml of acetonitrile and washed with 20 ml of diethyl ether. Thus 2.12 g of the desired compound are obtained, yield 61%, mp.: 211–214° C.

$C_{19}H_{12}N_4O_4$ (348.32) $^1$H NMR (($CD_3)_2$SO) δ 8.07 (1H, d, J=8.4 Hz), 7.75 (1H, d, J=1.8 Hz), 7.60 (1H, dd, J=8.4 Hz and J=1.8 Hz), 7.28 (1H, s), 6.88 (1H, s), 6.20 (1H, s), 6.15 (1H,s), 3.91 (1H, d, J=13.9 Hz), 3.18 (1H, d, J=13.8 Hz), 2.56 (3H, s).

EXAMPLE 19

5-(3-methyl-4-nitro-phenyl)-8-(semicarbazono-methyl)-9H-1,3-dioxolo[4,5-h][2,3]benzodiazepine A mixture of 3.51 g (10.0 millimoles) of 8-formyl-5-(3-methyl-4-nitro-phenyl)-9H-1,3-dioxolo[4,5-h][2,3]benzodiazepine, 1.34 g (12.0 millimoles) of semicarbazide hydrochloride, 1.01 g (12.0 millimoles) of anhydrous sodium acetate and 100 ml of anhydrous ethanol is stirred under boiling for 6 hours. The reaction mixture is evaporated in vacuo, the residue is suspended in 100 ml of water, stirred at room temperature for half an hour, filtered and washed with 25 ml of water. The crude product thus obtained is heated to boiling in 75 ml of acetone for half an hour, cooled with icecold water, the precipitated product is filtered and washed with 10 ml of cold acetone. Thus 3.34 g of the desired compound are obtained, yield 81%, mp.: 260–264° C.

$C_{19}H_{16}N_6O_5$ (408.38) $^1$H NMR (($CD_3)_2$SO) δ 10.63 (1H, S), 8.06 (1H, d, J=8.4 Hz), 7.42 (1H, d, J=1.4 Hz), 7.64 (1H, dd, J=8.4 Hz and J=1.7 Hz), 7.49 (1H, s), 7.26 (1H, S), 6.85 (2H, broad s), 6.77 (1H, s), 6.15 (1H, s), 6.08 (1H, S), 4.55 (1H, d, J=12.5 Hz), 2.63 (1H, d, J=12.4 Hz), 2.57 (3H, S).

EXAMPLE 20

7-acetyl-8-methyl-5-(3-methyl-4-nitro-phenyl)-7H-1,3-dioxolo[4,5-h][2.3]benzodiazepine A mixture of 3.37 g (10.0 millimoles) of 8-methyl-5-(3-methyl-4-nitro-phenyl)-9H-1,3-dioxolo[4,5-h][2,3]benzodiazepine and 25 ml acetyl chloride is stirred under boiling for 3 hours, whereupon the acid chloride is distilled off in vacuo. The residue is taken up in 100 ml of dichloro methane, washed with 50 ml of a saturated sodium carbonate solution and 50 ml of water. The organic phase is dried over magnesium sulfate and evaporated in vacuo. The crude product obtained is recrystallized from 50 ml of acetonitrile. Thus 2.62 g of the desired compound are obtained, yield 69%, mp.: 115–116° C.

$C_{20}H_{17}N_3O_5$ (379.38) $^1$H NMR (CDCl$_3$) δ 7.98 (1H, d, J=8.4 Hz), 7.52 (1H, d, J=1.8 Hz), 7.46 (1H, dd, J=8.4 Hz and J=1.8 Hz), 6.76 (1H, s), 6.52 (1H, s), 6.08 (1H, broad s), 6.03 (2H, broad s), 2.63 (3H, s), 2.28 (3H, s), 2.26 (3H, s).

EXAMPLE 21

7-(N-methyl-carbamoyl)-8-methyl-5-(3-methyl-4-nitro-phenyl)-7H-1.3-dioxolo[4,5-h][2,3]benzodiazepine 3.37 g (10.0 millimoles) of 8-methyl-5-(3-methyl-4-nitro-phenyl)-9H-1,3-dioxolo[4,5-h][2,3]benzodiazepine are dissolved in 75 ml of anhydrous dioxane, whereupon 2.35 g (1.89 ml, 15.0 millimoles) of phenyl chloro formate are added, and the reaction mixture is stirred on an oil bath having a temperature of 80° C. for 3 hours. The solvent is distilled off in vacuo and to the residue 30 ml of a 33% ethanolic methyl amine solution is added. The sealed flask is stirred at room temperature for an hour and evaporated. The residue is taken up in 100 ml of dichloro methane, washed twice with 50 ml of water each, dried over magnesium sulfate and evaporated in vacuo. The crude product obtained is crystallized from 75 ml of ethanol. Thus 2.44 g of the desired compound are obtained, yield 62%, mp.: 246–248° C.

$C_{20}H_{18}N_4O_5$ (394.39) $^1$H NMR (CDCl$_3$) δ 7.98 (1H, d, J=8.1 Hz), 7.43 (2H, m), 6.69 (1H, s), 6.42 (1H, s), 6.15 (1H, s), 6.09 (1H, m), 6.01 (2H, S), 2.96 (3H, d, J=4.4 Hz), 2.62 (3H, s), 2.21 (3H, s).

EXAMPLE 22

7-(N-cyclopropyl-carbamoyl)-8-methyl-5-(3-methyl-4-nitro-phenyl)-7H-1,3-dioxolo[4,5-h][2,3]benzodiazepine 3.37 g (10.0 millimoles) of 8-methyl-5-(3-methyl-4-nitro-phenyl)-9H-1,3-dioxolo[4,5-h][2,3]benzodiazepine are dissolved in 75 ml of anhydrous dioxane, 2.35 g (1.89 millimoles) of phenyl chloro formate are added and the reaction mixture is stirred on an oil bath having a temperature of 80° C. for an hour and a half. The solvent is distilled off in vacuo, to the residue 15 ml of cyclopropyl amine are added and the mixture is heated to boiling for 2 days. The excess of the amine is distilled off in vacuo. The residue is taken up in 100 ml of dichloro methane, washed twice with 50 ml of water, dried over magnesium sulfate and evaporated in vacuo. The crude product obtained is recrystallized from 45 ml of acetonitrile. Thus 2.98 g of the desired compound are obtained, yield 71%, mp.: 198–202° C.

$C_{22}H_{20}N_4O_5$ (420.43) $^1$H NMR (CDCl$_3$) δ 7.99 (1H, d, J=9.2 Hz), 7.42 (2H, m), 6.69 (1H, s), 6.41 (1H, s), 6.22 (1H, m), 6.15 (1H, s), 6.07 (2H, S), 2.77 (1H, m), 2.62 (3H, s), 2.21 (3H, s), 0.82 (2H, m), 0.62 (2H, m).

EXAMPLE 23

(±)-8-cyano-7,8-dihydro-8-methyl-5-(3-methyl-4-nitro-phenyl)-9H-1,3-dioxolo[4,5-h][2,3]benzodiazepine In a 100 ml bomb tube made of stainless steel 10.12 g (30.0 millimoles) of 8-methyl-5-(3-methyl-4-nitro-phenyl)-9H-1,3-dioxolo[4,5-h][2,3]benzodiazepine and 50 ml of glacial acetic acid are weighed in. To the suspension at 15–20° C. 5.90 g (90.6 millimoles) of potassium cyanide are added within 5 minutes under cooling with icecold water. The bomb tube is sealed. The reaction mixture is stirred at 70° C. for 24 hours, cooled, stirred with 350 ml of dichloro methane and 350 ml of water and the layers are separated. The aqueous phase is extracted with 150 ml of dichloro methane, the organic phases are washed with 50 ml of water, dried over magnesium sulfate and evaporated. The residue is is crystallized from 100 ml of ether, filtered and washed with ether. Thus 10.40 g of the desired compound are obtained, yield 95%, mp.: 148–151° C.

$C_{19}H_{16}N_4O_4$ (364.35)

EXAMPLE 24

(±)-7-acetyl-8-cyano-7, 8-dihydro-8-methyl-5-(3-methyl-4-nitro-phenyl)-9H-1,3-dioxolo[4,5-h][2,3]benzodiazepine To 60 ml of acetyl chloride 9.11 g (25.0 millimoles) of (±)-8-cyano-7,8-dihydro-8-methyl-5-(3-methyl-4-nitro-phenyl)-9H-1,3-dioxolo[4,5-h][2,3]benzodiazepine are added at 15° C. under stirring. The suspension formed turns into a solution within 5 minutes, but after a further period of 5 minutes a suspension is re-formed. The reaction mixture is stirred at 25° C. for 6 days, whereupon it is evaporated in vacuo. To the residue 90 ml of water are added and the mixture is stirred under cooling with icecold water for half an hour. The precipitated crystals are filtered and washed with icecold water. The crude product is crystallized from 150 ml of acetonitrile. The crystals are filtered, washed with acetonitrile and ether and dried. Thus 6.84 g of the desired compound are obtained, yield 67%, mp.: 253–255° C.

$C_{21}H_{18}N_4O_5$ (406.40) $^1$H NMR (CDCl$_3$) δ 8.01 (1H, d, J=9.0 Hz), 7.59 (2H, m), 6.99 (1H, s), 6.52 (1H, s), 6.10 (1H, d, J=1.3 Hz), 6.06 (1H, d, J=1.3 Hz), 3.08 (2H, s), 2.64 (3H, s), 2.28 (3H, S), 1.84 (3H, s).

EXAMPLE 25

(±)-8-cyano-7,8-dihydro-8-methyl-5-(3-methyl-4-nitro-phenyl)-7-propionyl-9H-1,3-dioxolo[4,5-h][2,3]benzodiazepine To 55 ml of propionyl chloride 7.06 g (19.4 millimoles) of (±)-8-cyano-7,8-dihydro-8-methyl-5-(3-methyl-4-nitro-phenyl)-9H-1,3-dioxolo[4,5-h][2,3]benzodiazepine are added at 15° C. The reaction mixture is stirred at 25° C. for 8 days and evaporated in vacuo. To the residue 200 ml of water are added. The mixture is stirred under cooling with icecold water for an hour. The precipitated crystals are filtered and washed with icecold water. The crude product obtained is recrystallized from 100 ml of acetonitrile. The crystals are filtered, washed with acetonitrile and ether and dried. Thus 6.30 g of the desired compound are obtained, yield 77%, mp.: 191–193° C.

$C_{22}H_{20}N_4O_5$ (420.41)

EXAMPLES 26–39

General Methods for the Reduction of the Nitro Group of Compounds Prepared According to Examples 1–25

Method A 5.0 millimoles of the nitro compound are dissolved in a mixture of 100 ml of dichloro methane and 50 ml of methanol. The solution is hydrogenated in the presence of 0.10 g of a 10% palladium charcoal catalyst at a pressure of 5.065·10$^5$ Pa. After hydrogenation the catalyst is filtered off, the filtrate is evaporated in vacuo and the crude product obtained is recrystallized.

Method B 3.45 g (25.0 millimoles) of potassium carbonate, 3.92 g (22.5 millimoles) of sodium dithionite and 0.14 g (0.25 milli-moles) of N,N'-bis-octadecyl-4,4'-bipyridinium-dibromide are dissolved in 100 ml of water, whereupon the solution or suspension of 5.0 millimoles of the nitro compound used as starting material formed with 100 ml of ethyl acetate is added under nitrogen. The reaction mixture is stirred at room temperature for 2–3 days and the layers are separated. The aqueous phase is extracted four times with 50 ml of ethyl acetate each. The united organic layers are washed with 50 ml of a saturated sodium chloride solution, dried over magnesium sulfate, filtered through a charcoal-bed and evaporated in vacuo. The crude product obtained is recrystallized.

Method C 6.8 millimoles of the nitro compound are suspended in a mixture of 130 ml of ethanol and 30 ml of water. To the suspension 1.5 g of a 10% palladium-charcoal catalyst are added, whereupon within 10 minutes 19.0 g (383.0 milli-moles) of 98% hydrazine hydrate are added. The reaction mixture warms to 36° C. and the starting material goes into solution. The reaction mixture is stirred at room temperature for two hours and a half, whereby the reaction mixture cools to 25° C. and the product precipitates. The catalyst is filtered off and washed twice with 100 ml of ethanol and twice with 200 ml of chloroform each. The filtrate is evaporated in vacuo. To the crystalline residue 300 ml of water are added, the mixture is stirred for an hour. The crystals are filtered and washed with water. The crude product thus obtained is recrystallized.

The characteristic data of the compounds thus obtained are summarized in the following Table I.

TABLE I

| No. of Example | Nomenclature of compound | Brutto formula | Cystallizing solvent, Mp. ° C. | Yield (%) |
|---|---|---|---|---|
| 26. | 5-(4-amino-3-methyl-phenyl)-9H-7,8-dihydro-8-methyl-1,3-dioxolo[4,5-h][2.3]benzodiazepine | $C_{18}H_{17}N_3O_2$ (307.36) | dimethyl-formamide 262–264 | 64 |
| Method: A | Elementary analysis calc.: found: | C 70.34 (%) 69.99 (%) | H 5.58 (%) 5.38 (%) | N 13.67 (%) 13.25 (%) |
| | $^1$H NMR ((CD$_3$)$_2$SO) δ 7.20 (1H, d, J=1.4 Hz), 7.10 (1H, dd, J=8.2 Hz and J=2.0 Hz), 7.03 (1H, s), 6.69 (1H, s), 6.62 (1H, s), 6.11 (1H, d, J=0.7 Hz), 6.05 (1H, s), 5.24 (2H, broad s), 3.34 (1H, d, J=12.0 Hz), 2.69 (1H, d, J=12.0 Hz), 2.07 (3H, s), 2.01 (3H, s). | | | |
| 27. | (±)-7-acetyl-5-(4-amino-3-methyl-phenyl)-7,8-dihydro-8-methyl-9H-1,3-dioxolo[4,5-h][2,3]benzodiazepine | $C_{20}H_{21}N_3O_3$ (351.41) | acetonitrile 121–123 | 75 |
| Method: A | Elementary analysis calc.: found: | C 68.36 (%) 67.51 (%) | H 6.02 (%) 5.81 (%) | N 11.96 (%) 12.16 (%) |
| | $^1$H NMR (CDCl$_3$) δ 7.47 (1H, s), 7.31 (1H, d, J=8.4 Hz), 6.76 (1H, s), 6.66 (1H, d, J=8.4 Hz), 6.58 (1H, s), 5.99 (2H, m), 5.22 (1H, m), 4.08 (2H, broad s), 2.66 (2H, m), 2.19 (3H, s), 2.01 (3H, s), 1.31 (3H, d, J=6.2 Hz). | | | |
| 28. | (±)-5-(3-methyl-4-amino-phenyl)-7,6-dihydro-8- | $C_{21}H_{23}N_3O_3$ (365.44) | acetonitrile 170–172 | 78 |

TABLE I-continued

| No. of Example | Nomenclature of compound | Brutto formula | Cystallizing solvent, Mp. ° C. | Yield (%) |
|---|---|---|---|---|
| | methyl-7-propionyl-9H-1,3-dioxolo[4,5-h]-[2,3]benzodiazepine | | | |

Method: Elementary analysis
A
calc.:   C 69.02 (%)   H 6.34 (%)   N 11.50 (%)
found:  C 69.00 (%)   H 6.28 (%)   N 11.23 (%)

$^1$H NMR (CDCl$_3$) δ 7.46 (1H, broad s), 7.33 (1H, dd, J=8.2 Hz and J=1.8 Hz), 6.76 (1H, s), 6.66 (1H, d, J=8.3 Hz), 6.57 (1H, s), 6.00 (1H, d, J=1.3 Hz), 5.95 (1H, d, J=1.3 Hz), 5.21 (1H, m), 4.05 (2H, broad s), 2.65 (2H, m), 2.47 (1H, m), 2.19 (1H, m), 2.18 (3H, s), 1.30 (3H, d, J=6.4 Hz), 1.03 (3H, t, J=7.5 Hz).

| No. of Example | Nomenclature of compound | Brutto formula | Cystallizing solvent, Mp. ° C. | Yield (%) |
|---|---|---|---|---|
| 29. | (±)-5-(4-amino-3-methyl-phenyl)-7-(N-cyclo-propyl-carbamoyl)-7,8-dihydro-8-methyl-9H-1,3-dioxolo[4,5-h][2,3]benzodiazepine | C$_{22}$H$_{24}$N$_4$O$_3$ (392.48) | diethyl ether 179–181 | 60 |

Method: Elementary analysis
B
calc.:   C 67.33 (%)   H 6.16 (%)   N 14.28 (%)
found:  C 67.29 (%)   H 6.13 (%)   N 14.10 (%)

$^1$H NMR (CDCl$_3$) δ 7.29 (1H, s), 7.23 (1H, dd, J=8.2 Hz and J=1.6 Hz), 6.72 (1H, s), 6.66 (1H, d, J=8.2 Hz), 6.57 (1H, s), 6.08 (1H, broad s), 5.98 (1H, s), 5.95 (1H, d, J=0.8 Hz), 5.16 (1H, m), 3.95 (2H, broad s), 2.81 (1H, dd, J=14.1 Hz and J=4.5 Hz), 2.64 (2H, m), 2.18 (3H, s), 1.15 (3H, d, J=6.3 Hz), 0.71 (2H, m), 0.51 (2H, m).

| No. of Example | Nomenclature of compound | Brutto formula | Cystallizing solvent, Mp. ° C. | Yield (%) |
|---|---|---|---|---|
| 30. | (±)-5-(4-amino-3-methyl-phenyl)-7,8-dihydro-8-methyl-7-(N-methozy-carbamoyl)-9H-1,3-dioxolo[4,5-h][2,3]benzodiazepine | C$_{20}$H$_{22}$N$_4$O$_4$ (382.42) | ethanol 150–152 | 78 |

Method: Elementary analysis
A
calc.:   C 62.82 (%)   H 5.80 (%)   N 14.65 (%)
found:  C 62.49 (%)   H 5.83 (%)   N 14.35 (%)

$^1$H NMR (CDCl$_3$) δ 8.30 (1H, s), 7.26 (1H, broad s), 7.25 (1H, dd, J=8.2 Hz and J=2.2 Hz), 6.75 (1H, s), 6.67 (1H, d, J=8.4 Hz), 6.59 (1H, s), 6.01 (1H, d, J=1.5 Hz), 5.98 (1H, d, J=1.5 Hz), 5.18 (1H, m), 3.77 (3H, s), 2.70 (2H, m), 2.20 (3H, s), 1.23 (3H, d, J=6.2 Hz).

| No. of Example | Nomenclature of compound | Brutto formula | Cystallizing solvent, Mp. ° C. | Yield (%) |
|---|---|---|---|---|
| 31. | (±)-5-(4-amino-3-methyl-phenyl)-7,8-dihydro-8-methyl-7-(N-methyl-carbamoyl)-9H-1,3-dioxolo[4.5-h][2,3]benzodiazepine | C$_{20}$H$_{22}$N$_4$O$_3$ (366.42) | acetonitrile 177–180 | 72 |

Method: Elementary analysis
A
calc.:   C 65.56 (%)   H 6.05 (%)   N 15.29 (%)
found:  C 64.91 (%)   H 6.03 (%)   N 14.98 (%)

$^1$H NMR (CDCl$_3$) δ 7.34 (1H, s), 7.25 (1H, dd, J=8.2 Hz and J=2.4 Hz), 6.73 (1H, s), 6.66 (1H, d, J=8.2 Hz), 6.58 (1H, s), 5.97 (1H, d, J=1.1 Hz), 5.95 (1H, d, J=1.1 Hz), 5.87 (1H, m), 5.17 (1H, m), 3.98 (2H, broad s), 2.84 (3H, d, J=4.8 Hz), 2.81 (1H, dd, J=14.2 Hz and J=4.7 Hz), 2.64 (1H, dd, J=14.0 Hz and J=10.2 Hz), 2.18 (3H, s), 1.15 (3H, d, J=6.3 Hz).

| No. of Example | Nomenclature of compound | Brutto formula | Cystallizing solvent, Mp. ° C. | Yield (%) |
|---|---|---|---|---|
| 32. | (±)-7-acetyl-5-(4-amino-3-methyl-phenyl-7,8-dihydro-9H-1,3-dioxolo[4,5-h][2,3]benzodiazepine-8-carboxylic acid-amid | C$_{20}$H$_{20}$N$_4$O$_4$ (380.41) | acetonitrile 177–180 | 72 |

Method: Elementary analysis
A
calc.:   C 63.15 (%)   H 5.30 (%)   N 14.73 (%)
found:  C 62.30 (%)   H 5.05 (%)   N 14.29 (%)

$^1$H NMR ((CD$_3$)SO δ 7.30 (1H, d, J=1.3 Hz), 7.18 (1H, dd, J=8.3 Hz and J=1.9 Hz), 7.07 (2H, broad s), 6.98 (1H, s), 6.64 (1H, d, J=8.4 Hz), 6.60 (1H, s), 6.10 (1H, d, J=0.6 Hz), 6.06 (1H, d, J=0.6 Hz), 5.51 (2H, broad s), 5.24 (1H, dd, J=12.3 Hz and J=5.0 Hz), 3.03 (1H, dd, J=13.7 Hz and J=5.0 Hz), 2.74 (1H, t, J=13.0 Hz), 2.08 (3H, s), 2.00 (3H, s).

| No. of Example | Nomenclature of compound | Brutto formula | Cystallizing solvent, Mp. ° C. | Yield (%) |
|---|---|---|---|---|
| 33. | 5-(4-amino-3-methyl-phenyl)-8-cyano-9H-1,3-dioxolo[4,5-h][2,3]benzodiazepine | C$_{18}$H$_{14}$N$_4$O$_2$ (318.34) | acetonitrile 252–255 | 54 |

Method: Elementary analysis
B
calc.:   C 67.92 (%)   H 4.43 (%)   N 17.60 (%)
found:  C 67.66 (%)   H 4.30 (%)   N 17.02 (%)

$^1$H NMR ((CD$_3$)SO δ 7.27 (1H, d, J=1.4 Hz), 7.19 (1H, s), 7.15 (1H, dd, J=8. Hz and J=1.8 Hz), 6.82 (1H, s), 6.65 (1H, d, J=8.4 Hz), 6.18 (1H, d, J=0.7 Hz), 6.12 (1H, d, J=0.7 Hz), 5.58 (2H, broad s), 3.75 (1H, d, J=13.6 Hz), 3.10 (1.H, d, J=13.6 Hz), 2.08 (3H, s).

| No. of Example | Nomenclature of compound | Brutto formula | Cystallizing solvent, Mp. ° C. | Yield (%) |
|---|---|---|---|---|
| 34. | 5-(4-amino-3-methyl-phenyl)-8-(semicarbazono-methyl)-9H-1,3-dioxolo[4,5-h][2,3]benzodiazepine | C$_{19}$H$_{18}$N$_5$O$_3$ (378.39) | acetonitrile 287–291 | 68 |

Method: Elementary analysis
A
calc:    C 60.31 (%)   H 4.79 (%)   N 22.21 (%)
found:   C 59.82 (%)   H 4.67 (%)   N 21.45 (%)

$^1$H NMR (CDCl$_3$) δ 10.54 (1H, s), 7.45 (1H, s), 7.20 (2H, m), 6.82 (2H, broad s), 6.72 (1H, s), 6.64 (1H, d, J=8.7 Hz), 6.13 (1H, s), 6.03 (1H, s), 5.38 (2H, broad s), 4.42 (1H, d, J=12.5 Hz), 2.56 (1H, d, J=12.5 Hz), 2.09 (3H, s).

| No. of Example | Nomenclature of compound | Brutto formula | Cystallizing solvent, Mp. ° C. | Yield (%) |
|---|---|---|---|---|
| 35. | 7-acetyl-5-(4-amino-3-methyl-phenyl)-8-methyl-7H-1,3-dioxolo[4,5-h][2,3]benzodiazepine | C$_{20}$H$_{19}$N$_3$O$_3$ (349.39) | acetonitrile 222–223 | 63 |

Method: Elementary analysis
B
calc.:   C 68.75 (%)   H 5.48 (%)   N 12.03 (%)
found:  C 68.43 (%)   H 5.42 (%)   N 11.80 (%)

$^1$H NMR (CDCl$_3$) δ 7.28 (1H, d, J=1.5 Hz), 7.13 (1H, dd, J=8.2 Hz and J=2.0 Hz), 6.73 (1H, s), 6.72 (1H, s), 6.63 (1H, d, J=8.2 Hz), 6.32 (1H, d, J=1.2 Hz), 6.03 (1H, d, J=1.1 Hz), 5.96 (1H, d, J=1.2 Hz), 3.90 (2H, broad s), 2.27 (3H, d, J=1.2 Hz), 2.23 (3H, s), 2.17 (3H, s).

| No. of Example | Nomenclature of compound | Brutto formula | Cystallizing solvent, Mp. ° C. | Yield (%) |
|---|---|---|---|---|
| 36. | 5-(4-amino-3-methyl-phenyl)-7-(N-methyl-carbamoyl)-8-methyl-7H-1,3-dioxolo-[4.5-h][2,3]benzodiazepine | C$_{20}$H$_{20}$N$_4$O$_3$ (36441) | tert.butyl methyl-ether 208–209 | 69 |

Method: Elementary analysis
B
calc.:   C 65.92 (%)   H 5.53 (%)   N 15.37 (%)
found:  C 65.07 (%)   H 5.48 (%)   N 14.81 (%)

$^1$H NMR (CDCl$_3$) δ 7.20 (1H, d, J=1.1 Hz), 7.10 (1H, dd, J=8.2 Hz and J=1.9 Hz), 6.66 (1H, s), 6.64 (1H, s), 6.63

TABLE I-continued

| No. of Example | Nomenclature of compound | Brutto formula | Cystallizing solvent, Mp. °C. | Yield (%) |
|---|---|---|---|---|
| | (1H, d, J=8.2 Hz), 6.13 (1H, s), 6.03 (1H, q, J=4.8 Hz), 6.00 (1H, broad s), 5.94 (1H, broad s), 3.90 (2H, broad s), 2.93 (3H, d, J=4.9 Hz), 2.21 (3H, s), 2.16 (3H, s). | | | |
| 37. | 5-(4-amino-3-methyl-phenyl-7-(N-cyclopropyl-carbamoyl)-8-methyl-7H-1,3-dioxolo-4,5-h][2,3] benzodiazepine | $C_{22}H_{22}N_4O_3$ (390.45) | ethanol 208–209 | 65 |

| Method: B | Elementary analysis | C | H | N |
|---|---|---|---|---|
| | calc.: | 67.68 (%) | 5.68 (%) | 14.35 (%) |
| | found: | 67.39 (%) | 5.69 (%) | 13.97 (%) |

$^1$H NMR (CDCl$_3$) δ 7.15 (1H, s), 7.08 (1H, dd, J=8.4 Hz and J=2.2 Hz), 6.67 (1H, s), 6.66 (1H, d, J=8.4 Hz), 6.64 (1H, s), 6.22 (1H, s), 6.13 (1H, s), 6.01 (1H, broad s), 5.95 (1H, broad s), 3.85 (2H, broad s), 2.72 (1H, m), 2.22 (3H, d, J=1.1 Hz), 2.17 (3H, s), 0.76 (2H, m), 0.60 (2H, m).

| 38. | (±)-7-acetyl-5-(4-amino-3-methyl-phenyl)-8-cyano-7,8-dihydro-8-methyl-9H-1,3-dioxolo[4,5-h][2,3]benzodiazepine | $C_{21}H_{20}N_4O_3$ (376.42) | ethyl-acetate 156–158 | 62 |

| Method: C | Elementary analysis | C | H | N |
|---|---|---|---|---|
| | calc.: | 67.01 (%) | 5.36 (%) | 14.88 (%) |
| | found: | 64.39 (%) | 5.55 (%) | 14.42 (%) |

$^1$H NMR (CDCl$_3$) δ 7.39 (1H, d, J=1.4 Hz), 7.30 (1H, dd, J=2.0 and 8.3 Hz), 6.96 (1H, s), 6.66 (1H, d, J=8.3 Hz), 6.64 (1H, s), 6.07 (1H, d, J=1.3 Hz), 6.01 (1H, d, J=1.3 Hz), 4.06 (2H, broad s), 3.03 (1H, d, J=14.0 Hz), 2.93 (1H, d, J=14.0 Hz), 2.18 (3H, s), 2.17 (3H, s), 1.81 (3H, s).

| 39. | (±)-5-(4-amino-3-methyl-phenyl)-8-cyano-7,8-dihydro-6-methyl-7-propionyl-9H-1,3-dioxolo[4,5-h][2,3]benzodiazepine monohydrate | $C_{22}H_{22}N_4O_3$ $H_2O$ (408.46) | diethyl ether 162–163 | 69 |

| Method: C | Elementary analysis | C | H | N |
|---|---|---|---|---|
| | calc.: | 64.69 (%) | 5.92 (%) | 13.72 (%) |
| | found: | 62.63 (%) | 5.62 (%) | 13.26 (%) |

$^1$H NMR (CDCl$_3$) δ 7.39 (1H, s), 7.31 (1H, d, J=8.2 Hz), 6.97 (1H, s), 6.67 (1H, d, J=8.3 Hz), 6.63 (1H, s), 6.07 (1H, s), 6.01 (1H, s), 4.06 (2H, broad s), 3.03 (1H, d, J=13.9 Hz), 2.92 (1H, d, J=13.6 Hz), 2.60 (1H, m), 2.56 (1H, m), 2.19 (3H, s), 1.81 (3H, s), 1.10 (3H, t, J=7.4 Hz).

The invention claimed is:

1. A compound of the Formula (I)

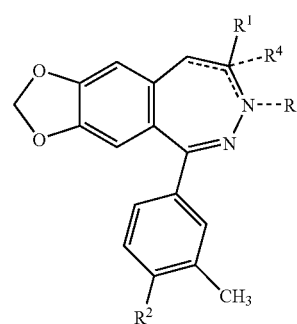

wherein
R$^1$ is methyl, formyl, carboxy, cyano, —CH═NOH, —CH═NNHCONH$_2$ or —CO—NR$^5$R$^6$, wherein
R$^5$ and R$^6$ independently from each other are hydrogen or lower alkyl or together with the nitrogen atom to which they are attached, form a 5- or 6-membered, saturated or unsaturated heterocyclic ring optionally containing one or more further nitrogen, sulfur and/or oxygen atoms;

R$^2$ is nitro or amino;

R$^3$ is hydrogen, lower alkanoyl, or —CONR$^7$R$^8$ wherein R$^7$ and R$^8$ independently from each other are hydrogen, lower alkoxy, lower alkyl, or lower cycloalkyl, or together with the nitrogen atom to which they are attached, form a 5- or 6-membered, saturated or unsaturated heterocyclic ring optionally containing one or more further nitrogen, sulfur and/or oxygen atoms;

R$^4$ is hydrogen or lower alkyl; and the dotted lines have the following meanings:
if R$^3$ and R$^4$ are not present, the bond between positions C$^8$ and C$^9$ is a single bond, and the bond between positions C$^8$ and N$^7$ is a double bond;
if R$^3$ and R$^4$ are present, the bonds between positions C$^8$ and C$^9$ and between positions C$^8$ and N$^7$ are single bonds; and
if R$^3$ is present and R$^4$ is missing, the bond between positions C$^8$ and C$^9$ is a double bond and the bond between positions C$^8$ and N$^7$ is a single bond;
or a pharmaceutically acceptable salt thereof.

2. A compound of the Formula (IA)

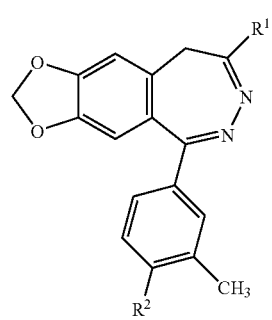

wherein
R¹ is methyl, formyl, carboxy, cyano, —CH=NOH, —CH=NNHCONH₂ or —CO—NR⁵R⁶, wherein
R⁵ and R⁶ independently from each other are hydrogen or lower alkyl or together with the nitrogen atom to which they are attached, form a 5- or 6-membered, saturated or unsaturated heterocyclic ring optionally containing one or more further nitrogen, sulfur and/or oxygen atoms; and
R² is nitro or amino;
or a pharmaceutically acceptable salt thereof.

3. A compound of the Formula (IB)

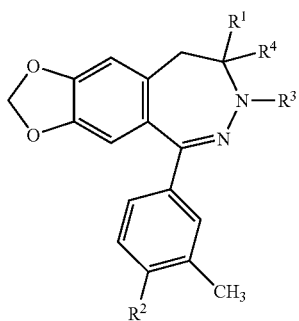

IB wherein
R¹ is methyl, formyl, carboxy, cyano, —CH=NOH, —CH=NNHCONH₂ or —CO—NR⁵R⁶, wherein
R⁵ and R⁶ independently from each other are hydrogen or lower alkyl or together with the nitrogen atom to which they are attached, form a 5- or 6-membered, saturated or unsaturated heterocyclic ring optionally containing one or more further nitrogen, sulfur and/or oxygen atoms;
R² is nitro or amino;
R³ is hydrogen, lower alkanoyl, or —CONR⁷R⁸ wherein
R⁷ and R⁸ independently from each other are hydrogen, lower alkoxy, lower alkyl, or lower cycloalkyl, or together with the nitrogen atom to which they are attached, form a 5- or 6-membered, saturated or unsaturated heterocyclic ring optionally containing one or more further nitrogen, sulfur and/or oxygen atoms; and
R⁴ is hydrogen or lower alkyl; or a pharmaceutically acceptable salt thereof.

4. A compound of the Formula (IC)

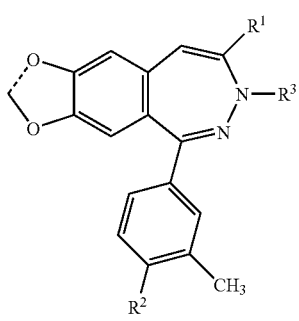

IC wherein
R¹ is methyl, formyl, carboxy, cyano, —CH=NOH, —CH=NNHCONH₂ or —CO—NR⁵R⁶, wherein
R⁵ and R⁶ independently from each other are hydrogen or lower alkyl or together with the nitrogen atom to which they are attached, form a 5- or 6-membered, saturated or unsaturated heterocyclic ring optionally containing one or more further nitrogen, sulfur and/or oxygen atoms;
R² is nitro or amino; and
R³ is hydrogen, lower alkanoyl, or —CONR⁷R⁸ wherein
R⁷ and R⁸ independently from each other are hydrogen, lower alkoxy, lower alkyl, or lower cycloalkyl, or together with the nitrogen atom to which they are attached, form a 5- or 6-membered, saturated or unsaturated heterocyclic ring optionally containing one or more further nitrogen, sulfur and/or oxygen atoms; or a pharmaceutically acceptable salt thereof.

5. The compound of the Formula (IA) defined in claim 2 wherein R² is amino; or a pharmaceutically acceptable salt thereof.

6. The compound of the Formula (IB) defined in claim 3 wherein R² is amino; or a pharmaceutically acceptable salt thereof.

7. The compound of the Formula (IC) defined in claim 4 wherein R² is amino; or a pharmaceutically acceptable salt thereof.

8. The compound of the Formula (IB) defined in claim 3 wherein R¹ is methyl or cyano; R² is amino; R³ is lower alkanoyl or —CONR⁷R⁸; R⁷ is hydrogen; R⁸ is lower alkyl, lower alkoxy, or lower cycloalkyl; and R⁴ is hydrogen or methyl; or a pharmaceutically acceptable salt thereof.

9. The compound of the Formula (IC) defined in claim 4 wherein R¹ is methyl; R² is amino; R³ is lower alkanoyl or —CONR⁷R⁸; R⁷ is hydrogen; and R⁸ is lower alkyl, lower alkoxy, or lower cycloalkyl; or a pharmaceutically acceptable salt thereof.

10. The compound of the Formula (IA) defined in claim 2 wherein R¹ is formyl, carboxy, cyano, —CH=NOH, —CH=NNHCONH₂ or —CO—NR⁵R⁶, or a pharmaceutically acceptable salt thereof.

11. The compound of the Formula (IA) defined in claim 10 which is 5-(4-amino-3-methyl-phenyl)-8-(semicarbazono-methyl)-9H-1,3-dioxolo-[4,5-H][2,3]benzodiazepine or a pharmaceutically acceptable salt thereof.

12. The compound of the Formula (IB) defined in claim 8 which is 7-acetyl-5-(4-amino-3-methyl-phenyl)-7,8-dihydro-8-methyl-9H-1,3-dioxolo[4,5-h][2,3]benzodiazepine; or a pharmaceutically acceptable salt thereof.

13. The compound of the Formula (IB) defined in claim 8 which is selected from the group consisting of:
5-(3-methyl-4-amino-phenyl)-7-propionyl-7,8-dihydro-8-methyl-9H-1,3-dioxolo[4,5-h][2,3]benzodiazepine;
5-(4-amino-3-methyl-phenyl)-7-(N-cyclopropyl-carbamoyl)-7,8-dihydro-8-methyl-9H-1,3-dioxolo[4,5-h][2,3]benzodiazepine;
5-(4-amino-3-methyl-phenyl)-7-(N-methoxy-carbamoyl)-7,8-dihydro-8-methyl-9H-1,3-dioxolo[4,5-h][2,3]benzodiazepine;
5-(4-amino-3-methyl-phenyl)-7-(N-methyl-carbamoyl)-7,8-dihydro-8-methyl-9H-1,3-dioxolo[4,5-h][2,3]benzodiazepine;
5-(4-amino-3-methyl-phenyl)-7-acetyl-8-cyano-7,8-dihydro-8-methyl-9H-1,3-dioxolo[4,5-h][2,3]benzodiazepine; and 5-(4-amino-3-methyl-phenyl)-8-cyano-7-propionyl-7,8-dihydro-8-methyl-9H-1,3-dioxolo[4,5-h][2,3]benzodiazepine;

or a pharmaceutically acceptable salt thereof.

14. The compound of the Formula (IC) defined in claim 9 selected from the group consisting of:

7-acetyl-5-(4-amino-3-methyl-phenyl)-8-methyl-7-H-1,3-dioxolo[4,5-h][2,3]-benzodiazepine;

7-(N-methyl-carbamoyl)-5-(4-amino-3-methyl-phenyl)-8-methyl-7H-1,3-dioxolo-[4,5-h][2,3]-benzodiazepine; and 7-(N-cyclopropyl-carbamoyl)-5-(4-amino-3-methyl-phenyl)-8-methyl-7H-1,3-dioxolo-[4,5-h][2,3]benzodiazepine; or a pharmaceutically acceptable salt thereof.

15. A pharmaceutical composition for treating epilepsy, stroke, Parkinson's disease, multiple sclerosis or amyotropic lateral sclerosis which comprises a therapeutically effective amount of a compound of the Formula (I)

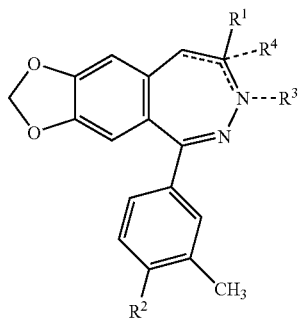

wherein $R^1$ is methyl, formyl, carboxy, cyano, —CH=NOH, —CH=NNHCONH$_2$ or —CO—NR$^5$R$^6$, wherein $R^5$ and $R^6$ independently from each other are hydrogen or lower alkyl or together with the nitrogen atom to which they are attached, form a 5- or 6-membered, saturated or unsaturated heterocyclic ring optionally containing one or more further nitrogen, sulfur and/or oxygen atoms;

$R^2$ is nitro or amino;

$R^3$ is hydrogen, lower alkanoyl, or —CONR$^7$R$^8$ wherein $R^7$ and $R^8$ independently from each other are hydrogen, lower alkoxy, lower alkyl, or lower cycloalkyl, or together with the nitrogen atom to which they are attached, form a 5- or 6-membered, saturated or unsaturated heterocyclic ring optionally containing one or more further nitrogen, sulfur and/or oxygen atoms;

$R^4$ is hydrogen or lower alkyl; and the dotted lines have the following meanings:

if $R^3$ and $R^4$ are not present, the bond between positions $C^8$ and $C^9$ is a single bond, and the bond between positions $C^8$ and $N^7$ is a double bond;

if $R^3$ and $R^4$ are present, the bonds between positions $C^8$ and $C^9$ and between positions $C^8$ and $N^7$ are single bonds; and if $R^3$ is present and $R^4$ is missing, the bond between positions $C^8$ and $C^9$ is a double bond and the bond between positions $C^8$ and $N^7$ is a single bond;

or a pharmaceutically acceptable salt thereof, and a pharmaceutically acceptable inert carrier.

16. A method of treating a mammalian subject in need of treatment for epilepsy, stroke, Parkinson's disease, multiple sclerosis or amyotropic lateral sclerosis which comprises the step of administering to said mammalian subject a therapeutically effective amount of a compound of the Formula (I) as defined in claim 1.

17. A process for the preparation of a compound of the Formula (I)

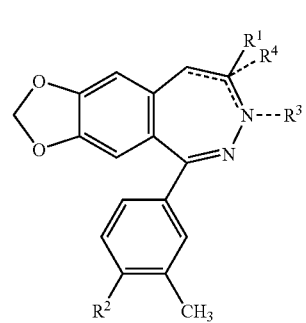

wherein $R^1$ is methyl, formyl, carboxy, cyano, —CH=NOH, —CH=NNHCONH$_2$ or —CO—NR$^5$R$^6$, wherein $R^5$ and $R^6$ independently from each other are hydrogen or lower alkyl or together with the nitrogen atom to which they are attached, form a 5- or 6-membered, saturated or unsaturated heterocyclic ring optionally containing one or more further nitrogen, sulfur and/or oxygen atoms;

$R^2$ is nitro or amino;

$R^3$ is hydrogen, lower alkanoyl, or —CONR$^7$R$^8$ wherein $R^7$ and $R^8$ independently from each other are hydrogen, lower alkoxy, lower alkyl, or lower cycloalkyl, or together with the nitrogen atom to which they are attached, form a 5- or 6-membered, saturated or unsaturated heterocyclic ring optionally containing one or more further nitrogen, sulfur and/or oxygen atoms;

$R^4$ is hydrogen or lower alkyl; and the dotted lines have the following meanings:

if $R^3$ and $R^4$ are not present, the bond between positions $C^8$ and $C^9$ is a single bond, and the bond between positions $C^8$ and $N^7$ is a double bond;

if $R^3$ and $R^4$ are present, the bonds between positions $C^8$ and $C^9$ and between positions $C^8$ and $N^7$ are single bonds; and if $R^3$ is present and $R^4$ is missing, the bond between positions $C^8$ and $C^9$ is a double bond and the bond between positions $C^8$ and $N^7$ is a single bond;

or a pharmaceutically acceptable salt thereof; which comprises:

a) for the preparation of 8-formyl-5-(3-methyl-4-nitrophenyl)-9H-1,3-dioxolo[4,5-h-][2,3]benzodiazepine of the Formula (III)

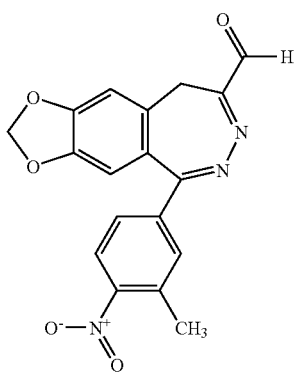

III oxidizing
8-methyl-5-(4-nitro-3-methyl-phenyl)-9H-1,3-dioxolo[4,5-h][2,3]benz odiazepine of the Formula (II)

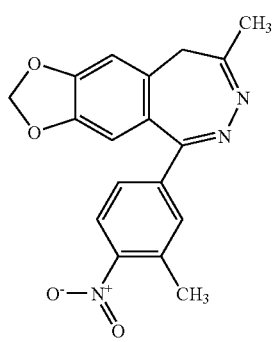

II or b) for the preparation of 5-(3-methyl-4-nitro-phenyl)-9H-1,3-dioxolo-[4,5-h][2,3]benzodiazepine-8-carboxylic acid of the Formula (IV)

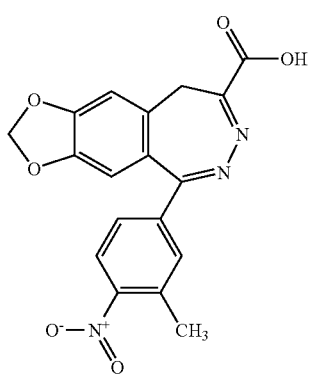

IV oxidizing the
8-formyl-5-(3-methyl-4-nitro-phenyl)-9H-1,3-dioxolo[4,5-h][2,3]benzodiazepine;

or c) for the preparation of a compound of the Formula (V)

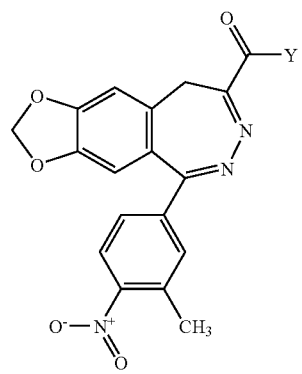

wherein Y is a leaving group, reacting the compound of the Formula IV with a compound capable of introducing group Y; or d) for the preparation of the compound of the Formula (VI)

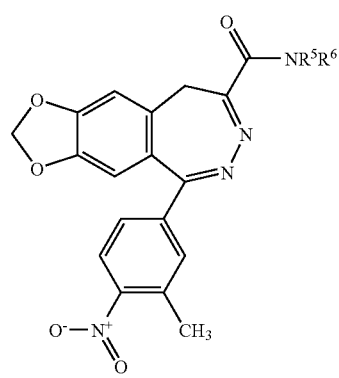

VI wherein $R^5$ and $R^6$ are as defined above, reacting the carboxylic acid of the Formula (IV) or a reactive derivative thereof of the Formula (V) with an amine of the Formula $HNR^5R^6$;

or e) for the preparation of a compound of the Formula (VII)

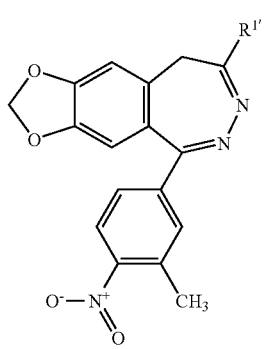

VII wherein $R^1$ is cyano, —CH=NOH or —CH=NNHCONH$_2$, converting in the compound of the Formula (III) the formyl group into an $R^1$ group; or f) for the preparation of a compound of the Formula (VIII)

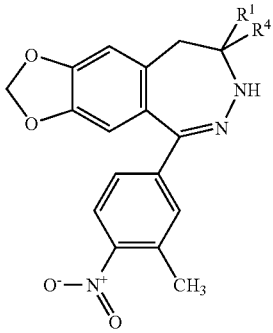

saturating the $C^8$—$N^7$ double bond of the compound of the Formula (VII) by addition or reduction;
or
g) for the preparation of a compound of the Formula (IX)

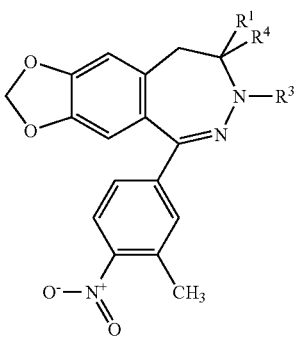

wherein $R^3$ is lower alkanoyl), reacting a compound of the Formula (VIII) with a compound capable of introducing a lower alkanoyl group;
or
h) for the preparation of a compound of the Formula (X)

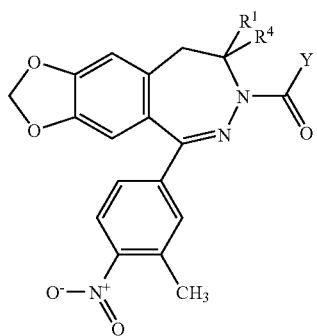

wherein Y is a leaving group and $R^1$ and $R^4$ are as stated above, reacting a compound of the Formula (VIII) with a compound capable of introducing the —COY group;

or
i) for the preparation of a compound of the Formula (XI)

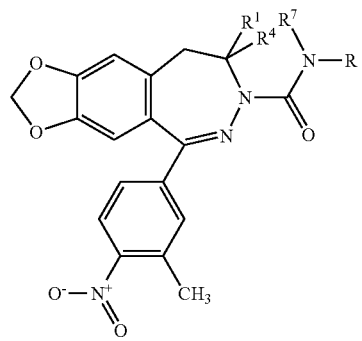

wherein $R^1$, $R^4$, $R^7$ and $R^8$ are as stated above, reacting a compound of the Formula (X) or the corresponding free carboxylic acid thereof with an amine of the Formula $HNR^7R^8$;
or
j) for the preparation of a compound of the Formula (XII)

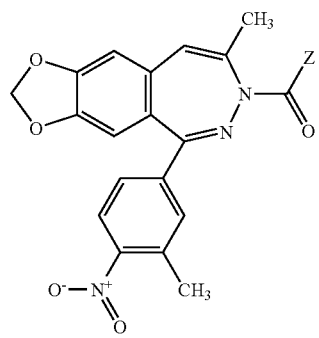

wherein Z is a leaving group, reacting the compound of the Formula (II) with a compound capable of introducing the —COZ group;
or
k) for the preparation of a compound of the Formula (XIII)

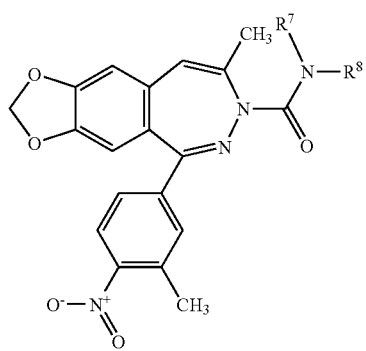

wherein $R^7$ and $R^8$ are as stated above, reacting a compound of the Formula (XII) with an amine of the Formula $HNR^7R^8$; or l) for the preparation of a compound of the Formula (I), wherein $R^2$ is amino, reducing the corresponding compound of the Formula (I), wherein $R^2$ is nitro; and, if desired, converting a compound of the Formula (I) into a pharmaceutically acceptable acid addition salt thereof or setting free a compound of the Formula (I) from a salt.

18. Process according to process 1) defined in claim 17 which comprises reducing as the compound of the Formula (I), a compound of the Formulae (II), (VII), (IX), (XI), (XII) or (XIII).

19. Process according to claim 18 which comprises carrying out the reduction by using stannous (II) chloride, sodium dithionite or by means of catalytic hydrogenation.

20. Process according to claim 19 in which the reduction is carried out by catalytic hydrogenation and which comprises using a Raney-nickel, palladium or platinum catalyst, and a hydrogen source selected from the group consisting of hydrogen, hydrazine, hydrazine hydrate, formic acid, trialkyl ammonium formate and an alkali formate.

21. A process for preparing a compound of the Formula (I)

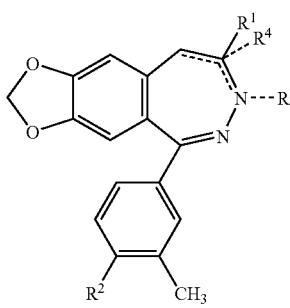

I wherein $R^1$ is methyl, formyl, carboxy, cyano, —CH=NOH, —CH=NNHCONH$_2$ or —CO—NR$^5$R$^6$, wherein
  $R^5$ and $R^6$ independently from each other are hydrogen or lower alkyl or together with the nitrogen atom to which they are attached, form a 5- or 6-membered, saturated or unsaturated heterocyclic ring optionally containing one or more further nitrogen, sulfur and/or oxygen atoms;

$R^2$ is amino;

$R^3$ is hydrogen, lower alkanoyl, or —CONR$^7$R$^8$ wherein
  $R^7$ and $R^8$ independently from each other are hydrogen, lower alkoxy, lower alkyl, or lower cycloalkyl, or together with the nitrogen atom to which they are attached, form a 5- or 6-membered, saturated or unsaturated heterocyclic ring optionally containing one or more further nitrogen, sulfur and/or oxygen atoms;

$R^4$ is hydrogen or lower alkyl; and the dotted lines have the following meanings:

if $R^3$ and $R^4$ are not present, the bond between positions $C^8$ and $C^9$ is a single bond, and the bond between positions $C^8$ and $N^7$ is a double bond;

if $R^3$ and $R^4$ are present, the bonds between positions $C^8$ and $C^9$ and between positions $C^8$ and $N^7$ are single bonds; and if $R^3$ is present and $R^4$ is missing, the bond between positions $C^8$ and $C^9$ is a double bond and the bond between positions $C^8$ and $N^7$ is a single bond;

or a pharmaceutically acceptable salt thereof; which comprises the step of reducing a compound of the Formula (I)

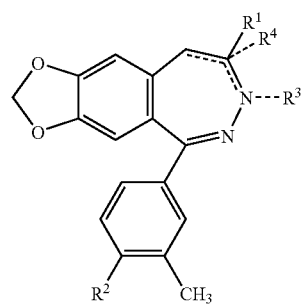

I wherein $R^2$ is nitro and $R^1$, $R^3$, $R^4$, $R^5$, $R^6$, $R^7$, $R^8$ and the dotted lines are as defined above with stannous (II) chloride, sodium dithionite or by catalytic hydrogenation.

* * * * *